(12) United States Patent
Beddard

(10) Patent No.: US 12,714,874 B2
(45) Date of Patent: Aug. 25, 2026

(54) PULSED ELECTROMAGNETIC FIELD SYSTEM

(71) Applicant: HOFMEIR MAGNETICS LIMITED, Reading (GB)

(72) Inventor: Paul Beddard, Herefordshire (GB)

(73) Assignee: HOFMEIR MAGNETICS LIMITED, Reading (GB)

( * ) Notice: Subject to any disclaimer, the term of this patent is extended or adjusted under 35 U.S.C. 154(b) by 369 days.

(21) Appl. No.: 18/271,797

(22) PCT Filed: Jan. 12, 2022

(86) PCT No.: PCT/GB2022/050058

§ 371 (c)(1),
(2) Date: Jul. 11, 2023

(87) PCT Pub. No.: WO2022/153043

PCT Pub. Date: Jul. 21, 2022

(65) Prior Publication Data

US 2024/0066312 A1 Feb. 29, 2024

(30) Foreign Application Priority Data

Jan. 12, 2021 (GB) ..................................... 2100369

(51) Int. Cl.
*A61N 5/06* (2006.01)
*H01F 7/20* (2006.01)
*H05B 45/32* (2020.01)

(52) U.S. Cl.
CPC ................ *A61N 5/06* (2013.01); *H01F 7/20* (2013.01); *H05B 45/32* (2020.01);
(Continued)

(58) Field of Classification Search
CPC .............. A61N 5/06; A61N 2005/0651; A61N 2005/0659; A61N 2005/0663;
(Continued)

(56) References Cited

U.S. PATENT DOCUMENTS

2009/0036952 A1 2/2009 Kao et al.
2020/0333438 A1* 10/2020 Petrov .................. H01S 5/0428

FOREIGN PATENT DOCUMENTS

GB 2262043 A 6/1993
WO 98/57704 A1 12/1998
(Continued)

OTHER PUBLICATIONS

International Search Report and Written Opinion, PCT/GB2022/050058, dated Apr. 25, 2022, 12 pgs.

*Primary Examiner* — Niketa Patel
*Assistant Examiner* — Sebastian X Lukjan
(74) *Attorney, Agent, or Firm* — Polsinelli PC

(57) ABSTRACT

The disclosure relates to a system including a pulsed electromagnetic field (EMF) device configured to generate an EMF pulse, and a second device. The second device includes a coil loop and a light generating unit electrically coupled to the coil loop. The coil loop is configured to induce a current in response to the EMF pulse. The light generating unit is arranged to receive at least some of the induced current and emit a light pulse having an intensity proportional to the received current.

17 Claims, 16 Drawing Sheets

(52) U.S. Cl.
CPC ................. *A61N 2005/0651* (2013.01); *A61N 2005/0659* (2013.01); *A61N 2005/0663* (2013.01); *A61N 2005/0667* (2013.01)

(58) Field of Classification Search
CPC .......... A61N 2005/0667; A61N 5/0613; A61N 2005/0632; A61N 2005/0645; A61N 2005/0662; A61N 1/40; A61N 2005/0652; H01F 7/20; H05B 45/32
See application file for complete search history.

(56) References Cited

FOREIGN PATENT DOCUMENTS

| | | | |
|---|---|---|---|
| WO | 99/42176 | A1 | 8/1999 |
| WO | 2018/071906 | A1 | 4/2018 |
| WO | 2019/097254 | A1 | 5/2019 |

* cited by examiner 26
57
21
64
24
22
25
53
53b
53a
65
55
56
56
55
50
54

PULSED ELECTROMAGNETIC FIELD SYSTEM

CROSS REFERENCE TO RELATED APPLICATIONS

This application is a United States National Stage Entry of PCT Application No. PCT/GB2022/050058 filed 12 Jan. 2022, which claims priority to Great Britain Application No. 2100369.4 filed 12 Jan. 2021, the contents of which are entirely incorporated by reference herein.

TECHNICAL FIELD

The present disclosure relates to systems and methods for generating pulsed electromagnetic fields, particularly, but not exclusively, for generating energy pulses for providing physiological effects on a human or animal body.

BACKGROUND

Light pulses can be used to provide a physiological effect on a human or animal body. For example light pulses can be applied to parts of the body to provide physiological effects on the skin or tissue below the skin. However, at present, light pulse therapy devices require a dedicated power source or power supply, which makes light therapy devices large and bulky.

Pulsed electromagnetic fields can also be used to provide physiological effects on the body. For example, pulsed electromagnetic fields can be used to provide therapeutic benefits, such as treating ailments like joint and muscle pain, and assisting with the healing of broken bones and fractures.

It is desirable to develop a system that overcomes or mitigates the problems associated with light pulse therapy devices, whilst improving the physiological effects and therapeutic benefits achievable with light pulses and pulsed electromagnetic fields.

SUMMARY OF THE DISCLOSURE

In a first aspect of the present disclosure, there is provided a system comprising:

a pulsed electromagnetic field (EMF) device configured to generate an EMF pulse; and a second device comprising:

a coil loop; and a light generating unit electrically coupled to the coil loop, wherein the coil loop is configured to induce a current in response to the EMF pulse, and wherein the light generating unit is arranged to receive at least some of the induced current and emit a light pulse having an intensity proportional to the received current.

Advantageously, the second device can emit a light pulse without requiring a separate power supply or power source. Rather, the second device is able to emit light using energy transferred from the pulsed EMF device via the EMF pulse. Furthermore, the current induced in the second device will naturally have a similar waveform or shape to the EMF pulse. As such, in exemplary embodiments, the induced current and consequently the light pulse, will be synchronised with the EMF pulse. In particular, the light pulse will comprise peaks in intensity that are time-synchronised with energy peaks of the EMF pulse. The synchronisation between the EMF pulse and light pulse has been found to enhance the respective physiological effects caused by the EMF pulse and the light pulse when the EMF pulse and the light pulse are provided to parts of a human or animal body.

In exemplary embodiments, the EMF pulse comprises a decaying sequence of electromagnetic (EM) oscillations.

Advantageously, this type of EMF pulse has been found to more effectively provide a physiological effect on the body.

In exemplary embodiments, the pulsed EMF device comprises an inductor configured to emit the EMF pulse, and the second device comprises means for mounting the second device to the pulsed EMF device such that the coil loop of the second device is inductively coupled with the inductor when the second device is mounted to the pulsed EMF device.

Advantageously, the pulsed EMF device and the second device can be provided as a combined unit to provide both a pulsed EMF and light pulses to the body. For example, the pulsed EMF device and the second device can comprise separate housings, and the housing of the second device can detachably mount to the housing of the pulsed EMF device as a modular attachment. This gives the user or operator the choice of providing a pulsed EMF treatment or a combination of a pulsed EMF and light pulses. Furthermore, the inductive coupling between the inductor and the coil loop provides for efficient means of energy transfer between the pulsed EMF device and the second device, in the absence of a power source or a power supply in the second device.

In exemplary embodiments, the mounting means is for mounting the second device to the inductor of the pulsed EMF device such that the coil loop of the second device is inductively coupled with the inductor when the second device is mounted to the inductor.

Advantageously, this arrangement has been found to further improve the efficiency of energy transfer between the pulsed EMF device and the second device given the closer proximity between the coil loop and the inductor. Furthermore, the pulsed EMF device and the second device can be provided as a single unit in a more compact form. For example, both the second device and the pulsed EMF device can be contained within a unitary common housing in which the second device is mounted to the inductor of the pulsed EMF device. Alternatively, the pulsed EMF device and the second device can be comprised in separate housings, but the inductor can be external to the housing of the pulsed EMF device to enable the second device to mount to the inductor.

In exemplary embodiments, the second device further comprises a rectifier coupled between the coil loop and the light generating unit, and the rectifier is configured to at least partly rectify the induced current.

Advantageously, rectifying the induced current has been found to improve the safety of the second device and prevent damage to the components of the light generating unit.

In exemplary embodiments, the second device further comprises an interface circuit coupled between the rectifier and the light generating unit, and the interface circuit is configured to condition the waveform of the induced current and output a conditioned current, wherein the light generating unit receives the conditioned current.

Advantageously, controlling the waveform of the induced current will in turn control the light output of the light generating unit. As such, the interface circuit can be used to control or tune how the light generating unit responds to the induced current by conditioning the induced current. It will be appreciated that in some exemplary embodiments, the rectifier may be omitted and the interface circuit may be coupled between the coil loop and the light generating unit.

In exemplary embodiments, the interface circuit comprises:

a low pass filter coupled between the rectifier and the light generating unit, the low pass filter configured to filter a first portion of the induced current to output a low frequency component of the conditioned current comprising a smooth pulse over the duration of the EMF pulse; and a resistive path between the rectifier and the light generating unit in parallel with the low pass filter, the resistive path arranged to conduct a second portion of the induced current to output a high frequency component of the conditioned current comprising a sequence of peaks synchronised with or corresponding to oscillations of the EMF pulse.

Consequently, the light pulse will comprise a combination of a low frequency component (a smooth pulse over the duration of the EMF pulse) and a high frequency component (a sequence of peaks synchronised with or corresponding to oscillations of the EMF pulse). Advantageously, the high frequency component has been found to contribute to providing an enhanced physiological effect in combination with the EMF pulse. By also including the low frequency component, the light pulse will be observed by the human eye as a single "blink". Therefore, the low frequency component may protect the human eye from the sharp flashes caused by the high frequency component, thereby improving the safety of the system. It will be appreciated that in some exemplary embodiments, the rectifier may be omitted. The low pass filter may be coupled between the coil loop and the light generating unit. Furthermore the resistive path may be between the coil loop and the light generating unit in parallel with the low pass filter.

In exemplary embodiments:

the rectifier comprises at least one diode having an anode coupled to a first side of the coil loop, and a cathode;

the low pass filter comprises a first resistor, a second resistor and a capacitor, wherein the first resistor is coupled between the cathode of the diode and the second resistor, the second resistor is coupled between the first resistor and a first side of the light generating unit, and the capacitor coupled between a common node between the first and the second resistors and a second side of the light generating unit; and the resistive path comprises a third resistor coupled between the cathode of the diode and the first side of the light generating unit.

Advantageously, values of the first resistor and the capacitor can be chosen to set the cut-off frequency of the low-pass filter so that the low pass filter outputs the desired low-frequency component. Furthermore, the value of the second resistor can be chosen to determine the overall current output of the low-pass filter, and thus the overall brightness of the light pulse. Furthermore, the value of the third resistor can be chosen to determine the amplitude or brightness of the high-frequency peaks.

In exemplary embodiments, the light generating unit comprises at least one light-emitting diode (LED).

Advantageously, the light generating unit can be implemented cost effectively whilst taking up a smaller circuit area.

In exemplary embodiments, the LED is configured to emit infrared or red light.

Advantageously, infrared or red visible light has been found to enhance the physiological effect provided by the light pulse.

In exemplary embodiments, the coil loop is a first coil loop and the induced current is a first current.

In exemplary embodiments, the second device comprises a second coil loop electrically coupled to the light generating unit. The second coil loop is configured to induce a second current in response to the EMF pulse. The light generating unit is arranged to receive at least some of the first current and the second current. Furthermore, the first coil loop is in a first plane and the second coil loop may be in a second plane that is different to the first plane.

Advantageously, optimal power transfer between the coil looped inductor and the second device can be maintained when the coil looped inductor is angled relative the second device. In particular, current from both the first and the second coil loops can contribute to powering the light therapy device when the coil looped inductor is not at an optimal orientation or position relative to the light therapy device.

In exemplary embodiments, the first plane and the second plane intersect.

Advantageously, the first plane is angled relative to the second plane. This enables improved power transfer between the coil looped inductor and the second device for a range of relative angles and positions between the coil looped inductor and the coil loops of the second device.

In exemplary embodiments, the first plane and the second plane are substantially orthogonal or perpendicular to one another.

Advantageously, an approximate 90 degree angle may be the most optimal angle between the planes for improved power transfer during use.

In exemplary embodiments, the rectifier is a first rectifier.

In exemplary embodiments, the second device further comprises a second rectifier coupled between the second coil loop and the light generating unit. The second rectifier is configured to at least partly rectify the second current.

Advantageously, the second current is rectified which further improves the safety of the second device whilst preventing damage to the components of the light generating unit.

In exemplary embodiments, the interface circuit is configured to condition the waveform of a sum of the first current and the second current.

Advantageously, the interface circuit is used to control or tune how the light generating unit responds to the sum of the induced currents by conditioning the sum of the currents.

In exemplary embodiments, the second device comprises a third coil loop electrically coupled to the light generating unit. The third coil loop is configured to induce a third current in response to the EMF pulse, and the light generating unit is arranged to receive at least some of the first current, the second current and the third current. The third coil loop is in a third plane different to the first plane and the second plane. Optionally, the third plane intersects with the first plane and the second plane. Optionally, the first second and third planes are orthogonal to each other.

Advantageously, the third coil loop can further improve the angular independence of the light therapy device. For example, the light therapy device may achieve improved power transfer from the pulsed EMF device for a wider range of orientations and positions of the coil looped inductor.

In exemplary embodiments, the second device comprises means for attaching the second device to a part of a human or an animal body.

Advantageously, the second device can be used as a wearable device. For example, the second device can be secured at a predetermined position on the body part that is to receive light therapy and/or combined light and pulsed EMF therapy.

In exemplary embodiments, the pulsed EMF device further comprises:

- a parallel resonant circuit comprising a capacitor connected in parallel with an inductor without a switch between the capacitor and the inductor in the parallel resonant circuit, wherein the parallel resonant circuit is configured to generate the EMF pulse in the inductor while electrical energy is stored in the parallel resonant circuit, and wherein the inductor is configured to be placed relative to a part of a body to provide the pulsed electromagnetic field to the part of the body;
- a power source; and
- a switch, external to the parallel resonant circuit, which is configured to: selectively connect the parallel resonant circuit to the power source for a current ramping period during which a current in the inductor is increased to reach a desired current, and at the end of the current ramping period disconnect the parallel resonant circuit from the power source by opening the switch, wherein the parallel resonant circuit generates the sequence of damped electromagnetic oscillations in the inductor whilst the switch is open.

Advantageously, unlike other pulsed electromagnetic field therapy devices, the pulsed electromagnetic field therapy device has a parallel resonant circuit which does not require a switch (such as a semiconductor or spark gap switch) to be an integral component of the parallel resonant circuit to selectively power the parallel resonant circuit. By having a switch external to the parallel resonant circuit instead, when current flows around the parallel resonant circuit, it does not pass through a switch on each pass which would unnecessarily dissipate energy stored in the parallel resonant circuit through resistance losses in the switch. Moreover, suitable high voltage switches which can be used as a component of the parallel resonant circuit of a pulsed electromagnetic field therapy device are expensive. Therefore, by having a switch external to the parallel resonant circuit rather than as a component of the parallel resonant circuit, manufacturing costs are significantly reduced and resistance losses from the switch are eliminated. Without these resistance losses from the switch, the decay time of the pulsed electromagnetic field generated by the parallel resonant circuit is greatly increased, thereby increasing the time period over which a physiological effect is generated. Moreover, an increased decay time of the pulsed electromagnetic field allows for increased power transfer to the second device. Also, the desired current required to obtain a desired time period over which a physiological effect is achieved is much less.

Moreover, by having a switch external to the parallel resonant circuit rather than as a component of the parallel resonant circuit, it is possible to ramp the current over a period of time (the current ramping period). In contrast, other pulsed electromagnetic field therapy devices with a switch as a component of the parallel resonant circuit cause charge from the pre-charged capacitor to be dumped nearly instantaneously into the resonant circuit when the switch in the parallel resonant circuit is closed. The high voltages which are necessary to achieve the high currents needed to overcome resistance losses in the high voltage switch, cause a surge of current in the resonant circuit as soon as the switch is closed. This sudden surge in current in the resonant circuit has been found to result in reflections from the high voltage switch (which intrinsically lacks impedance matching with the resonant circuit) resulting in significant voltage and current spikes and electromagnetic interference which can be harmful to nearby electrical devices. In contrast, increasing the current over the current ramping period, which is made possible by the switchless parallel resonant circuit of the exemplary embodiment, reduces noise and interference caused by the pulsed electromagnetic field therapy device, which helps the pulsed electromagnetic field therapy device meet regulatory requirements, such as regulations regarding electromagnetic interference. For example, the pulsed electromagnetic field therapy device can be operated at lower frequencies than other devices, therefore preventing the pulsed electromagnetic field therapy device from interfering with other electronic devices such as the second device, or with radio communications networks. Additionally, a cleaner (e.g. less noisy) waveform of the pulsed electromagnetic field has been found to allow for improved and more efficient power transfer to the second device.

In a second aspect of the present disclosure, there is provided a method comprising:

- providing a coil loop for inductively coupling to an inductor of a pulsed EMF device;
- generating an EMF pulse in the inductor;
- inducing a current in the coil loop in response to the EMF pulse;
- receiving at least some of the induced current at a light generating unit electrically coupled to the coil loop; and
- emitting a light pulse from the light generating unit in response to the received current, the light pulse having an intensity proportional to the received current.

In exemplary embodiments, the coil loop is inductively coupled to the inductor of the pulsed EMF device.

In exemplary embodiments, the EMF pulse comprises a decaying sequence of electromagnetic (EM) oscillations.

In exemplary embodiments, the method further comprises rectifying the induced current using a rectifier coupled in between the coil loop and the light generating unit.

In exemplary embodiments, the method further comprises conditioning the waveform of the induced current using an interface circuit coupled between the rectifier and the light generating unit, and receiving the conditioned current at the light generating unit.

In exemplary embodiments, conditioning the waveform of the induced current comprises low-pass filtering a portion of the induced current using a low pass filter coupled between the rectifier and the light generating unit, to generate a low frequency component of the conditioned current comprising a smooth pulse over the duration of the EMF pulse.

In exemplary embodiments, conditioning the waveform of the induced current comprises passing a portion of the induced current through a resistive path provided between the rectifier and the light generating unit in parallel with the low-pass filter, to generate a high frequency component of the conditioned current comprising a sequence of peaks synchronised with or corresponding to oscillations of the EMF pulse.

In exemplary embodiments, the amplitude or duration of the low frequency component is dependent on a value of one or more resistors of the low pass filter; and/or the amplitude of the high-frequency component is dependent on a value of a resistor in the resistive path.

In exemplary embodiments, the light pulse is emitted from at least one light-emitting diode (LED) of the light generating unit.

In exemplary embodiments, the light pulse is infrared or red light.

In exemplary embodiments, the coil loop is a first coil loop and the induced current is a first current.

In exemplary embodiments, the method further comprises: providing a second coil loop for inductively coupling to the inductor of the pulsed EMF device; inducing a second current in the second coil loop in response to the EMF pulse; and receiving at least some of the first current and the second current at the light generating unit, wherein the first coil loop is provided in a first plane and the second coil loop is provided in a second plane that is different to the first plane.

In exemplary embodiments, the first plane and the second plane intersect.

In exemplary embodiments, the first plane and the second plane are substantially orthogonal or perpendicular to one another.

In exemplary embodiments, the rectifier is a first rectifier.

In exemplary embodiments, the method further comprises at least partly rectifying the second current using a second rectifier coupled in between the second coil loop and the light generating unit.

In exemplary embodiments, the method further comprises conditioning the waveform of a sum of the first current and the second current using an interface circuit coupled between the first and the second rectifiers and the light generating unit and receiving the conditioned current at the light generating unit.

In exemplary embodiments, the method further comprises providing a third coil loop for inductively coupling to the inductor of the pulsed EMF device. The third coil loop is induces a third current in response to the EMF pulse, and the light generating unit receives at least some of the first current, the second current and the third current. The third coil loop is in a third plane that is different to the first plane and the second plane. Optionally, the third plane intersects with the first plane and the second plane. Optionally, the first, second and third planes are orthogonal or perpendicular to one another.

In exemplary embodiments, the inductor is comprised in a switchless parallel resonant circuit, and wherein generating the EMF pulse comprises:

- ramping a current in the inductor of the switchless parallel resonant circuit to reach a desired current by connecting the parallel resonant circuit with a power supply over a current ramping period; and
- after the current ramping period, generating a sequence of damped electromagnetic oscillations in the inductor by disconnecting the parallel resonant circuit from the power supply.

In a third aspect of the present disclosure, there is provided a device comprising:

- a coil loop arranged to inductively couple to an inductor of a pulsed EMF device; and
- a light generating unit electrically coupled to the coil loop,
- wherein the coil loop is configured to induce a current in response to an EMF pulse generated by the inductor coil, and
- wherein the light generating unit is arranged to receive at least some of the induced current and emit a light pulse having an intensity proportional to the received current.

In exemplary embodiments, the device is for mounting to a pulsed electromagnetic field (EMF) device.

In exemplary embodiments, the first coil loop is arranged to inductively couple to the inductor of the pulsed EMF device when the device is mounted on the pulsed EMF device.

In exemplary embodiments, the device comprises means for mounting the device to the inductor of the pulsed EMF device such that the coil loop of the device is inductively coupled with the inductor when the second device is mounted to the inductor.

In exemplary embodiments, the device further comprises:

- a rectifier coupled between the coil loop and the light generating unit, the rectifier configured to at least partly rectify the induced current; and
- optionally, an interface circuit coupled between the rectifier and the light generating unit, the interface circuit configured to condition the waveform of the induced current, wherein the light generating unit receives the conditioned current.

In exemplary embodiments, the interface circuit comprises:

- a low pass filter coupled between the rectifier and the light generating unit, the low pass filter configured to output a low frequency component of the conditioned current comprising a smooth pulse over the duration of the EMF pulse; and
- a resistive path between the rectifier and the light generating unit in parallel with the low pass filter, the resistive path arranged to output a high frequency component of the conditioned current comprising a sequence of peaks synchronised with or corresponding to oscillations of the EMF pulse, optionally wherein:

- the rectifier comprises at least one diode having an anode coupled to a first side of the coil loop, and a cathode;
- the low pass filter comprises a first resistor, a second resistor and a capacitor, wherein the first resistor is coupled between the cathode of the diode and the second resistor, the second resistor is coupled between the first resistor and a first side of the light generating unit, and the capacitor coupled between a common node between the first and the second resistors and a second side of the light generating unit; and
- the resistive path comprises a third resistor coupled between the cathode of the diode and the first side of the light generating unit.

In exemplary embodiments, the coil loop is a first coil loop and the induced current is a first current.

In exemplary embodiments, the device comprises a second coil loop electrically coupled to the light generating unit,

- wherein the second coil loop is configured to induce a second current in response to the EMF pulse,
- wherein the light generating unit is arranged to receive at least some of the first current and the second current,
- wherein the first coil loop is in a first plane and the second coil loop is in a second plane that is different to the first plane,
- optionally wherein the first plane and the second plane intersect and/or wherein the first plane and the second plane are substantially orthogonal or perpendicular to one another.

In exemplary embodiments, the rectifier is a first rectifier.

In exemplary embodiments the device comprises a second rectifier coupled between the second coil loop and the light generating unit, the second rectifier configured to at least partly rectify the second current,

- optionally wherein the interface circuit is configured to condition the waveform of a sum of the first current and the second current.

In exemplary embodiments the device comprises a third coil loop electrically coupled to the light generating unit. The third coil loop is configured to induce a third current in response to the EMF pulse, and the light generating unit is arranged to receive at least some of the first current, the second current and the third current. The third coil loop is in a third plane different to the first plane and the second plane, optionally wherein the third plane intersects with the first plane and the second plane.

In exemplary embodiments, the device comprises means for attaching the second device to a part of a human or an animal body.

In another aspect of the present disclosure, there is provided a system comprising a pulsed electromagnetic field (EMF) device configured to generate an EMF pulse, and a second device.

In exemplary embodiments, the second device comprises a coil loop.

In exemplary embodiments, the second device comprises a light generating unit electrically coupled to the coil loop.

In exemplary embodiments, the coil loop is configured to induce a current in response to the EMF pulse.

In exemplary embodiments, the light generating unit is arranged to receive at least some of the induced current and emit a light pulse having an intensity proportional to the received current.

In exemplary embodiments, the EMF pulse comprises a decaying sequence of electromagnetic (EM) oscillations.

In exemplary embodiments, the EMF pulse comprises a decaying sequence of sinusoidal electromagnetic oscillations.

In exemplary embodiments, the EMF pulse comprises a decaying sequence of electromagnetic oscillations, wherein the oscillations have a square, triangle, saw-tooth, or any other shaped waveform.

In exemplary embodiments, the pulsed EMF device comprises an inductor configured to emit the EMF pulse.

In exemplary embodiments, the second device comprises means for mounting the second device to the pulsed EMF device such that the coil loop of the second device is inductively coupled with the inductor when the second device is mounted to the pulsed EMF device.

In exemplary embodiments, the second device comprises mounting means for mounting the second device to the inductor of the pulsed EMF device such that the coil loop of the second device is inductively coupled with the inductor when the second device is mounted to the inductor.

In exemplary embodiments, the pulsed EMF device and the second device are comprised in the same housing.

In exemplary embodiments, the pulsed EMF device and the second device are comprised in separate respective housings.

In exemplary embodiments, the pulsed EMF device and the second device are comprised in separate housings, and the inductor of the pulsed EMF device is external to the housing of the pulsed EMF device.

In exemplary embodiments, the second device further comprises a rectifier coupled between the coil loop and the light generating unit, and configured to at least partly rectify the induced current.

In exemplary embodiments, the rectifier is a half-wave rectifier configured to half-wave rectify the induced current.

In exemplary embodiments, the rectifier is a full-wave rectifier configured to full-wave rectify the induced current.

In exemplary embodiments, the full-wave rectifier is one of a bridge rectifier or a centre-tapped coil rectifier.

In exemplary embodiments, the second device further comprises an interface circuit coupled between the rectifier and the light generating unit.

In exemplary embodiments, the rectifier may be omitted and the interface circuit is coupled between the coil loop and the light generating unit.

In exemplary embodiments, the interface circuit is configured to condition the waveform of the induced current and output a conditioned current.

In exemplary embodiments, the light generating unit receives the conditioned current.

In exemplary embodiments, the interface circuit comprises a low pass filter coupled between the rectifier and the light generating unit.

In exemplary embodiments, the rectifier may be omitted and the low pass filter is coupled between the coil loop and the light generating unit.

In exemplary embodiments, the low pass filter is configured to filter a first portion of the induced current to output a low frequency component of the conditioned current.

In exemplary embodiments, the low frequency component comprises a smooth pulse over the duration of the EMF pulse.

In exemplary embodiments, the interface circuit comprises a resistive path between the rectifier and the light generating unit.

In exemplary embodiments, the rectifier may be omitted and the resistive path is between the coil loop and the light generating unit.

In exemplary embodiments, the interface circuit is in parallel with the low pass filter.

In exemplary embodiments, the resistive path is arranged to conduct a second portion of the induced current to output a high frequency component of the conditioned current.

In exemplary embodiments, the high frequency component comprises a sequence of peaks synchronised with oscillations of the EMF pulse.

In exemplary embodiments, the high frequency component comprises a sequence of peaks corresponding to oscillations of the EMF pulse.

In exemplary embodiments, the rectifier comprises at least one diode having an anode coupled to a first side of the coil loop, and a cathode.

In exemplary embodiments, the rectifier comprises a plurality of diodes.

In exemplary embodiments, the low pass filter comprises a first resistor, a second resistor and a capacitor.

In exemplary embodiments, the first resistor is coupled between the cathode of the diode and the second resistor.

In exemplary embodiments, the second resistor is coupled between the first resistor and a first side of the light generating unit.

In exemplary embodiments, the capacitor is coupled between a common node between the first and the second resistors and a second side of the light generating unit.

In exemplary embodiments, the resistive path comprises a third resistor coupled between the cathode of the diode and the first side of the light generating unit.

In exemplary embodiments, wherein the light generating unit comprises at least one light-emitting diode (LED).

In exemplary embodiments, the LED is configured to emit infrared or red light.

In exemplary embodiments, the coil loop comprises one or more turns.

In exemplary embodiments the pulsed EMF device further comprises a parallel resonant circuit.

In exemplary embodiments, the parallel resonant circuit comprises a capacitor connected in parallel with an inductor without a switch between the capacitor and the inductor in the parallel resonant circuit.

In exemplary embodiments, the parallel resonant circuit is configured to generate the EMF pulse in the inductor while electrical energy is stored in the parallel resonant circuit.

In exemplary embodiments, the inductor is configured to be placed relative to a part of a body to provide the pulsed electromagnetic field to the part of the body.

In exemplary embodiments, the pulsed EMF device comprises a power source.

In exemplary embodiments, the pulsed EMF device comprises a switch.

In exemplary embodiments, the switch is external to the parallel resonant circuit.

In exemplary embodiments, the switch is configured to selectively connect the parallel resonant circuit to the power source for a current ramping period during which a current in the inductor is increased to reach a desired current.

In exemplary embodiments, the switch is further configured to, at the end of the current ramping period, disconnect the parallel resonant circuit from the power source by opening the switch, wherein the parallel resonant circuit generates the sequence of damped electromagnetic oscillations in the inductor whilst the switch is open.

In exemplary embodiments, a charge stored in the capacitor before the switch external to the parallel resonant circuit is closed is zero.

In exemplary embodiments, the current ramping period is one of: greater than 1 μs; greater than 10 μs; between 1 μs and 50 μs; between 10 μs and 50 μs; between 1 μs and 100 μs; and between 10 μs and 100 μs.

In exemplary embodiments, the desired current is in the range of one of: 10 A and 2000 A; 100 A and 2000 A; 200 A and 2000 A; 200 A and 1600 A; 500 A and 1600 A; and 500 A and 2000 A.

In exemplary embodiments, the pulsed electromagnetic field has a frequency of one of: less than 1 MHz; less than 250 KHz; less than 200 KHz and less than 100 KHz.

In exemplary embodiments, the switch external to the parallel resonant circuit is open while the parallel resonant circuit is generating at least a portion of the pulsed electromagnetic field.

In exemplary embodiments, the inductor is a coil loop inductor.

In exemplary embodiments, the parallel resonant circuit is galvanically isolated from the power source.

In exemplary embodiments, the switch external to the parallel resonant circuit receives switching signals over an optical link, for example, a fibre optic cable.

In exemplary embodiments, the pulsed EMF device further comprises a further switch to selectively couple the parallel resonant circuit back to a capacitor of the power supply, wherein closing the further switch recharges the power supply capacitor from the parallel resonant circuit.

In exemplary embodiments, the further switch couples the parallel resonant circuit to the power supply when the current in the parallel resonant circuit is below a current threshold.

In exemplary embodiments, the duty cycle of the switch is 5% or less, or 1% or less.

In exemplary embodiments, the pulsed EMF device is a pulsed EMF therapy device.

In exemplary embodiments, the second device is a light therapy device.

In exemplary embodiments, the second device does not comprise a power source or power supply.

In exemplary embodiments, the coil loop is a first coil loop and the induced current is a first current.

In exemplary embodiments, the second device comprises a second coil loop electrically coupled to the light generating unit.

In exemplary embodiments, the second coil loop is configured to induce a second current in response to the EMF pulse.

In exemplary embodiments, the light generating unit is arranged to receive at least some of the first current and the second current.

In exemplary embodiments, the light generating unit is arranged to receive at least some of a sum of the first current and the second current.

In exemplary embodiments, the first coil loop is in a first plane and the second coil loop is in a second plane that is different to the first plane.

In exemplary embodiments, the first plane and the second plane intersect.

In exemplary embodiments, the first plane and the second plane are substantially orthogonal or perpendicular to one another.

In exemplary embodiments, the rectifier is a first rectifier.

In exemplary embodiments, the second device further comprises a second rectifier coupled between the second coil loop and the light generating unit.

In exemplary embodiments, the second rectifier is configured to at least partly rectify the second current.

In exemplary embodiments, the interface circuit is configured to condition the waveform of a sum of the first current and the second current.

In exemplary embodiments, the first coil loop and the first rectifier are coupled in series between a first common node and a second common node.

In exemplary embodiments, the second coil loop and the second rectifier are coupled in series between the first common node and the second common node.

In exemplary embodiments, the series combination of the first coil loop and the first rectifier is coupled in parallel with the series combination of the second coil loop and the second rectifier.

In exemplary embodiments, the first coil loop has a first number of turns and the second coil loop has a second number of turns.

In exemplary embodiments, the first number of turns is different to the second number of turns.

In exemplary embodiments, the first number of turns is the same as the second number of turns.

In exemplary embodiments, the second device comprises a third coil loop electrically coupled to the light generating unit.

In exemplary embodiments, the third coil loop is configured to induce a third current in response to the EMF pulse.

In exemplary embodiments, the light generating unit is arranged to receive at least some of the first current, the second current and the third current.

In exemplary embodiments, the light generating unit is arranged to receive at least some of a sum of the first current, the second current and the third current.

In exemplary embodiments, the third coil loop is in a third plane different to the first plane and the second plane.

In exemplary embodiments, the third plane intersects with the first plane and the second plane.

In exemplary embodiments, the first, second and third planes are substantially orthogonal to one another. Optionally, the third plane may be angled at substantially 90 degrees relative to the first plane and angled at substantially 90 degrees relative to the second plane.

In exemplary embodiments, the second device further comprises a third rectifier coupled between the third coil loop and the light generating unit.

In exemplary embodiments, the third rectifier is configured to at least partly rectify the third current.

In exemplary embodiments, the interface circuit is configured to condition the waveform of a sum of the first current, the second current and the third current.

In exemplary embodiments, the third coil loop and the third rectifier are coupled in series between the first common node and the second common node.

In exemplary embodiments, the second device is a wearable device.

In exemplary embodiments, the second device comprises means for attaching the second device to a part of a human or an animal body.

In another aspect of the present disclosure, there is provided a method comprising: providing a coil loop for inductively coupling to an inductor of a pulsed EMF device; generating an EMF pulse in the inductor; and inducing a current in the coil loop in response to the EMF pulse.

In exemplary embodiments, the first coil loop is inductively coupled to the inductor of the pulsed EMF device.

In exemplary embodiments, the method further comprises receiving at least some of the induced current at a light generating unit electrically coupled to the coil loop.

In exemplary embodiments, the method further comprises emitting a light pulse from the light generating unit in response to the received current.

In exemplary embodiments, the light pulse has an intensity proportional to the received current.

In exemplary embodiments, the EMF pulse comprises a decaying sequence of electromagnetic (EM) oscillations.

In exemplary embodiments, the EMF pulse comprises a decaying sequence of sinusoidal electromagnetic oscillations.

In exemplary embodiments, the EMF pulse comprises a decaying sequence of electromagnetic oscillations, wherein the oscillations have a square, triangle, saw-tooth, or any other shaped waveform.

In exemplary embodiments, the method further comprises at least partly rectifying the induced current using a rectifier.

In exemplary embodiments, the rectifier is coupled in between the coil loop and the light generating unit.

In exemplary embodiments, the rectifier is a half-wave rectifier configured to half-wave rectify the induced current.

In exemplary embodiments, the rectifier is a full-wave rectifier configured to full-wave rectify the induced current.

In exemplary embodiments, the full-wave rectifier is one of a bridge rectifier or a centre-tapped coil rectifier.

In exemplary embodiments, the method further comprises conditioning the waveform of the induced current using an interface circuit.

In exemplary embodiments, the interface circuit is coupled between the rectifier and the light generating unit.

In exemplary embodiments, the rectifier may be omitted and the interface circuit is coupled between the coil loop and the light generating unit.

In exemplary embodiments, the method comprises receiving the conditioned current at the light generating unit.

In exemplary embodiments, conditioning the waveform of the induced current comprises low-pass filtering a portion of the induced current using a low pass filter.

In exemplary embodiments, the low-pass filter is coupled between the rectifier and the light generating unit.

In exemplary embodiments, the rectifier may be omitted and the low pass filter is coupled between the coil loop and the light generating unit.

In exemplary embodiments, the low-pass filter generates a low frequency component of the conditioned current.

In exemplary embodiments, the low-frequency component comprises a smooth pulse over the duration of the EMF pulse.

In exemplary embodiments, conditioning the waveform of the induced current further comprises passing a portion of the induced current through a resistive path.

In exemplary embodiments, the resistive path is provided between the rectifier and the light generating unit.

In exemplary embodiments, the rectifier may be omitted and the resistive path is between the coil loop and the light generating unit In exemplary embodiments, the resistive path is also in parallel with the low-pass filter.

In exemplary embodiments, the resistive path generates a high frequency component of the conditioned current.

In exemplary embodiments, the high frequency component comprises a sequence of peaks synchronised with oscillations of the EMF pulse.

In exemplary embodiments, the high frequency component comprises a sequence of peaks corresponding to oscillations of the EMF pulse.

In exemplary embodiments, the amplitude or duration of the low frequency component is dependent on a value of one or more resistors of the low pass filter.

In exemplary embodiments, the overall amplitude of the high-frequency component is dependent on a value of a resistor in the resistive path.

In exemplary embodiments, the light pulse is emitted from at least one light-emitting diode (LED) of the light generating unit.

In exemplary embodiments, the light pulse is infrared or red light.

In exemplary embodiments, the inductor of the pulsed EMF device is comprised in a switchless parallel resonant circuit.

In exemplary embodiments, generating the EMF pulse comprises ramping a current in the inductor of the switchless parallel resonant circuit to reach a desired current by connecting the parallel resonant circuit with a power supply over a current ramping period.

In exemplary embodiments, generating the EMF pulse further comprises, after the current ramping period, generating a sequence of damped electromagnetic oscillations in the inductor by disconnecting the parallel resonant circuit from the power supply.

In exemplary embodiments, the pulsed EMF has a maximum current between 100 A and 2000 A and a maximum voltage between 150V and 2000V.

In exemplary embodiments, the pulsed electromagnetic field is generated by ramping a current in an inductor with a power supply having a voltage of between 50 V and 400 V.

In exemplary embodiments, the current in the inductor is ramped over a period of one of: greater than 1 μs; greater than 10 μs; between 1 μs and 50 μs; between 10 μs and 50 μs; between 1 μs and 100 μs; and between 10 μs and 100 μs.

In exemplary embodiments, the pulsed electromagnetic field is generated to have a decay time of at least: 100 μs; 200 μs; 300 μs; 400 μs; 500 μs; 600 μs; 700 μs; 800 μs; 900 μs; 1000 μs; 1100 μs; 1200 μs; 1300 μs; 1400 μs; 1500 μs; 1600 μs; 1700 μs; 1800 μs; 1900 μs; and 2000 μs.

In exemplary embodiments, the pulsed electromagnetic field has a frequency of one of: less than 1 MHz; less than 250 KHz, less than 200 KHz, and less than 100 KHz.

In exemplary embodiments, the duty cycle of the pulsed electromagnetic field is 5% or less, or 1% or less.

In exemplary embodiments, the coil loop is a first coil loop and the induced current is a first current.

In exemplary embodiments, the method further comprises providing a second coil loop for inductively coupling to the inductor of the pulsed EMF device.

In exemplary embodiments, the method further comprises inducing a second current in the second coil loop in response to the EMF pulse.

In exemplary embodiments, the method further comprises receiving at least some of the first current and the second current at the light generating unit.

In exemplary embodiments, the method further comprises receiving at least some of a sum of the first current and the second current at the light generating unit.

In exemplary embodiments, the first coil loop is provided in a first plane and the second coil loop is provided in a second plane that is different to the first plane.

In exemplary embodiments, the first plane and the second plane intersect.

In exemplary embodiments, the first plane and the second plane are substantially orthogonal or perpendicular to one another.

In exemplary embodiments, the rectifier is a first rectifier.

In exemplary embodiments, the method further comprises at least partly rectifying the second current using a second rectifier coupled in between the second coil loop and the light generating unit.

In exemplary embodiments, the method further comprises conditioning the waveform of a sum of the first current and the second current using an interface circuit coupled between the first and the second rectifiers and the light generating unit.

In exemplary embodiments, the method further comprises receiving the conditioned current at the light generating unit.

In exemplary embodiments, the method further comprises providing a third coil loop for inductively coupling to the inductor of the pulsed EMF device.

In exemplary embodiments, the method further comprises inducing a third current in the third coil loop in response to the EMF pulse.

In exemplary embodiments, the method further comprises receiving at least some of the first current, the second current and the third current at the light generating unit.

In exemplary embodiments, the method further comprises receiving at least some of a sum of the first current, the second current and the third current at the light generating unit.

In exemplary embodiments, the third coil loop is in a third plane that is different to the first plane and the second plane.

In exemplary embodiments, the third plane intersects with the first plane and the second plane.

In exemplary embodiments, the first, second and third planes are substantially orthogonal to one another.

In exemplary embodiments, the method further comprises at least partly rectifying the third current using a third rectifier coupled in between the third coil loop and the light generating unit.

In exemplary embodiments, the method further comprises conditioning the waveform of a sum of the first current, the second current and the third current using the interface circuit.

In another aspect of the present disclosure, there is provided a device comprising: a coil loop arranged to inductively couple to an inductor of a pulsed EMF device.

In exemplary embodiments, the device is for mounting to a pulsed electromagnetic field (EMF) device.

In exemplary embodiments, the first coil loop is arranged to inductively couple to the inductor of a pulsed EMF device when the device is mounted on the pulsed EMF device.

In exemplary embodiments, the device further comprises a light generating unit electrically coupled to the coil loop.

In exemplary embodiments, the coil loop is configured to induce a current in response to an EMF pulse generated by the inductor coil.

In exemplary embodiments, the light generating unit is arranged to receive at least some of the induced current and emit a light pulse having an intensity proportional to the received current.

In exemplary embodiments, the device comprises means for mounting the device to the inductor of the pulsed EMF device such that the coil loop of the device is inductively coupled with the inductor when the second device is mounted to the inductor.

In exemplary embodiments, the device comprises a housing.

In exemplary embodiments, the device further comprises a rectifier coupled between the coil loop and the light generating unit, and configured to at least partly rectify the induced current.

In exemplary embodiments, the rectifier is a half-wave rectifier configured to half-wave rectify the induced current.

In exemplary embodiments, the rectifier is a full-wave rectifier configured to full-wave rectify the induced current.

In exemplary embodiments, the full-wave rectifier is one of a bridge rectifier or a centre-tapped coil rectifier which may comprise a centre-tapped coil and rectifiers (e.g. diodes).

In exemplary embodiments, the device further comprises an interface circuit coupled between the rectifier and the light generating unit.

In exemplary embodiments, the rectifier may be omitted and the interface circuit is coupled between the coil loop and the light generating unit.

In exemplary embodiments, the interface circuit is configured to condition the waveform of the induced current.

In exemplary embodiments the light generating unit receives the conditioned current.

In exemplary embodiments the interface circuit comprises a low pass filter coupled between the rectifier and the light generating unit.

In exemplary embodiments, the rectifier may be omitted and the low pass filter is coupled between the coil loop and the light generating unit.

In exemplary embodiments, the low pass filter is configured to output a low frequency component of the conditioned current.

In exemplary embodiments, the low-frequency component comprises a smooth pulse over the duration of the EMF pulse.

In exemplary embodiments the interface circuit comprises a resistive path between the rectifier and the light generating unit.

In exemplary embodiments, the rectifier may be omitted and the resistive path is between the coil loop and the light generating unit.

In exemplary embodiments the resistive path is in parallel with the low pass filter.

In exemplary embodiments the resistive path is arranged to output a high frequency component of the conditioned current.

In exemplary embodiments the high frequency component comprises a sequence of peaks synchronised with oscillations of the EMF pulse.

In exemplary embodiments, the high frequency component comprises a sequence of peaks corresponding to oscillations of the EMF pulse.

In exemplary embodiments, the rectifier comprises at least one diode having an anode coupled to a first side of the coil loop, and a cathode.

In exemplary embodiments, the low pass filter comprises a first resistor, a second resistor and a capacitor.

In exemplary embodiments, the first resistor is coupled between the cathode of the diode and the second resistor.

In exemplary embodiments, the second resistor is coupled between the first resistor and a first side of the light generating unit.

In exemplary embodiments the capacitor is coupled between a common node between the first and the second resistors and a second side of the light generating unit.

In exemplary embodiments, the resistive path comprises a third resistor.

In exemplary embodiments, the third resistor is coupled between the cathode of the diode and the first side of the light generating unit.

In exemplary embodiments, the coil loop is a first coil loop and the induced current is a first current.

In exemplary embodiments, the device comprises a second coil loop electrically coupled to the light generating unit.

In exemplary embodiments, the coil loop is configured to induce a second current in response to the EMF pulse.

In exemplary embodiments, the light generating unit is arranged to receive at least some of the first current and the second current.

In exemplary embodiments, the light generating unit is arranged to receive at least some of a sum of the first current and the second current.

In exemplary embodiments, the first coil loop is in a first plane and the second coil loop is in a second plane that is different to the first plane.

In exemplary embodiments, the first plane and the second plane intersect.

In exemplary embodiments, the first plane and the second plane are substantially orthogonal or perpendicular to one another.

In exemplary embodiments, the rectifier is a first rectifier.

In exemplary embodiments, the device further comprises a second rectifier coupled between the second coil loop and the light generating unit.

In exemplary embodiments, the second rectifier configured to at least partly rectify the second current.

In exemplary embodiments, the interface circuit is configured to condition the waveform of a sum of the first current and the second current.

In exemplary embodiments, the first coil loop and the first rectifier are coupled in series between a first common node and a second common node.

In exemplary embodiments, the second coil loop and the second rectifier are coupled in series between the first common node and the second common node.

In exemplary embodiments, the series combination of the first coil loop and the first rectifier is coupled in parallel with the series combination of the second coil loop and the second rectifier.

In exemplary embodiments, the first coil loop has a first number of turns and the second coil loop has a second number of turns.

In exemplary embodiments, the first number of turns is different to the second number of turns.

In exemplary embodiments, the first number of turns is the same as the second number of turns.

In exemplary embodiments, the device comprises a third coil loop electrically coupled to the light generating unit.

In exemplary embodiments, the third coil loop is configured to induce a third current in response to the EMF pulse.

In exemplary embodiments, the light generating unit is arranged to receive at least some of the first current, the second current and the third current.

In exemplary embodiments, the light generating unit is arranged to receive at least some of a sum of the first current, the second current and the third current.

In exemplary embodiments, the third coil loop is in a third plane different to the first plane and the second plane.

In exemplary embodiments, the third plane intersects with the first plane and the second plane.

In exemplary embodiments, the first, second and third planes are substantially orthogonal to one another. Optionally, the third plane is angled at substantially 90 degrees relative to the first plane and angled at substantially 90 degrees relative to the second plane.

In exemplary embodiments, the device further comprises a third rectifier coupled between the third coil loop and the light generating unit.

In exemplary embodiments, the third rectifier is configured to at least partly rectify the third current.

In exemplary embodiments, the interface circuit is configured to condition the waveform of a sum of the first current, the second current and the third current.

In exemplary embodiments, the third coil loop and the third rectifier are coupled in series between the first common node and the second common node.

In exemplary embodiments, the device is a wearable device.

In exemplary embodiments, the device comprises means for attaching the second device to a part of a human or an animal body.

BRIEF DESCRIPTION OF THE DRAWINGS

Examples of the present disclosure are now described with reference to the accompanying drawings, in which.

DETAILED DESCRIPTION

The present disclosure relates to a system that emits a pulsed electromagnetic field (EMF) to a part of the human or animal body (e.g. a limb or a joint), whilst simultaneously emitting a series of light pulses to a part of the body. In particular, the systems emits the light pulses using energy harvested from the pulsed EMF. The system can be provided as a single unit or device. The system incorporates a pulsed EMF therapy device and a light therapy device. The pulsed EMF device is configured to generate the pulsed EMF, whereby each pulse includes a sequence of damped sinusoidal electromagnetic oscillations. The pulsed EMF is emitted by a coil looped inductor of the pulsed EMF device. The coil looped inductor is arranged to be placed adjacent to or around a part of the body, for example, to produce a physiological effect on the body. Circuitry of the light therapy device is inductively or magnetically coupled to the coil looped inductor of the pulsed EMF device. As such, the pulsed EMF generated in the coil looped inductor causes currents and voltages to be induced in the circuitry of the light therapy device. The light therapy device comprises one or more light emitting diodes (LEDs) that are arranged to emit light in response to the induced currents and voltages. The LEDs are arranged to be placed adjacent to or around a part of the body to provide the emitted light to the body, for example, to also produce a physiological effect on the body.

Advantageously, the light therapy device can operate without the need for a separate power supply or power source, and instead uses energy transferred from the coil looped inductor via the pulsed EMF. In other words, the light therapy device is able to operate using energy harvested from the pulsed EMF emitted by the pulsed EMF device, without the need for a separate power source such as a battery, or connection to a mains electricity supply. As such, the light therapy device can be provided in a smaller and more compact form, for example in a combined unit with the pulsed EMF device, or as a separate wearable device. Furthermore, due to the inductive coupling, the waveforms of the currents and voltages induced in the light therapy device will be synchronised with the energy waveform of the pulsed EMF. This means that the light pulses emitted by the LEDs will have an intensity or brightness that is synchronised with the energy or power level of the pulsed EMF. Advantageously, the synchronisation between the light pulses and the pulsed EMF has been found to enhance the respective physiological effects provided by the light pulse and the pulsed EMF, especially where the light pulses and the pulsed EMF are provided to the same part of the body.

Figure 1:
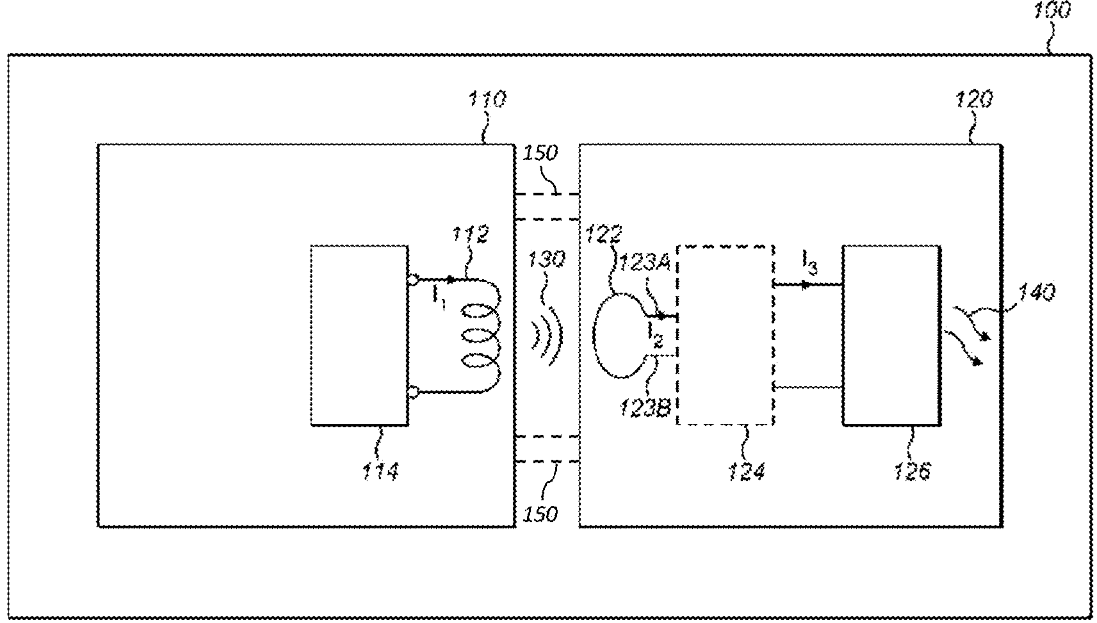
FIG. 1 shows a system comprising a pulsed electromagnetic field therapy device and a light therapy device according to an example of the present disclosure.

FIG. 1 shows a system 100 according to an example of the present disclosure. The system 100 comprises a pulsed electromagnetic field (PEMF) therapy device 110 and a light therapy device 120. The PEMF therapy device 110 is configured to generate and emit a pulsed electromagnetic field (EMF) 130. The light therapy device 120 is configured to emit light 140 in response to the pulsed EMF 130. In particular, the light therapy device 120 is configured to convert the pulsed EMF 130 into electrical energy and generate the light 140 based on the electrical energy. Advantageously, the light therapy device 120 is able to emit the light 140 based on the pulsed EMF 130, without requiring a separate power source or a power supply. As shown in FIG. 1, the PEMF therapy device 110 and the light therapy device 120 are connected by a mounting means 150 (e.g., a clip for connecting the PEMF therapy device 100 and the light therapy device 120).

The PEMF device 110 comprises a coil looped inductor 112 and a current generating circuit 114. The coil looped inductor 112 is electrically coupled to the current generating circuit 114. The current generating circuit 114 is configured to generate and supply a current $I_1$ to the coil looped inductor 112. The coil looped inductor 112 is configured to generate the pulsed EMF 130 in response to the current $I_1$. The coil looped inductor 112 is arranged in the device 110 to be placed adjacent to or around a part of a human or animal body (e.g. a limb or joint), in order to provide the pulsed EMF to that part of the body and produce a physiological effect.

Figure 4:
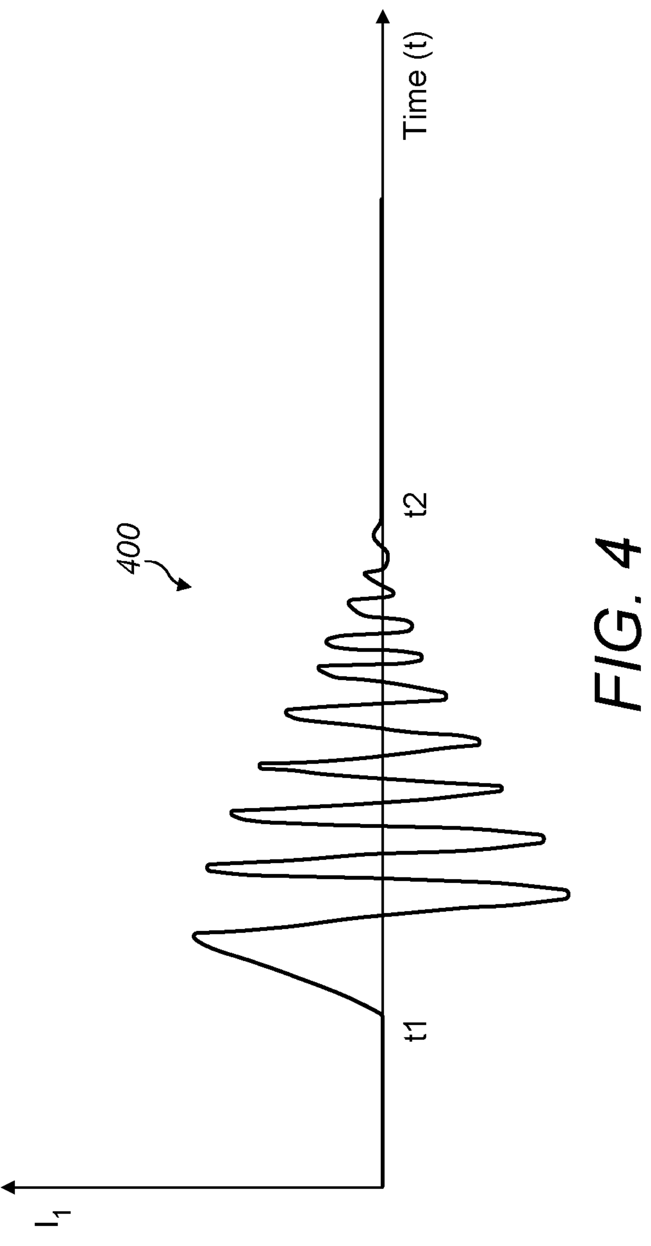
FIG. 4 shows an oscilloscope trace showing a current through an inductor of the pulsed electromagnetic field therapy device of the system of FIG. 1, as a function of time.

FIG. 4 illustrates an oscilloscope trace 400 showing the current $I_1$ as a function of time t. As shown, the current $I_1$ is an alternating current (AC) having a decaying sinusoidal shape. In other words, the current $I_1$ comprises a sequence of decaying or damped sinusoidal oscillations. The sequence of oscillations start at time $t_1$ and end at time t2. The current $I_1$ may have a peak value of 100 Amps, 1500 Amps, or any value within the range 100-1500 Amps. Furthermore, the length of time between times $t_1$ and $t_2$ may be 1 millisecond, 2 milliseconds, or any length of time between 1 and 2 milliseconds.

The coil looped inductor 112 is configured to generate an EMF that is proportional to the current $I_1$. In particular, the EMF generated by the coil looped inductor 112 will be an alternating EMF comprising a sequence of decaying or damped sinusoidal electromagnetic field oscillations. As such, the energy waveform of the generated EMF may correspond to the trace 400 shown in FIG. 4. The sequence of decaying sinusoidal electromagnetic oscillations, e.g. as shown in FIG. 4, may correspond to one pulse of the pulsed EMF 130. As such, the pulsed EMF 130 may comprise a series of electromagnetic pulses, each pulse comprising a sequence of damped sinusoidal oscillations. The current generating circuit 114 may be configured to provide the current $I_1$ such that it repeats the shape 400 shown in FIG. 4 in a series, so that the coil looped inductor 112 generates and emits a series of electromagnetic pulses comprising a sequence of damped sinusoidal oscillations.

Example implementations of the pulsed EMF device 110 are described in more detail below.

Reference is made back to FIG. 1. The light therapy device 120 comprises a coil loop 122, a conditioning circuit 124 and a light generating unit 126. The coil loop 122 comprises a first terminal 123A and a second terminal 123B.

The conditioning circuit 124 is electrically coupled to the coil loop 122. In particular, the conditioning circuit 124 is electrically coupled to the terminals 123A, 123B of the coil loop 122. The light generating unit 126 is electrically coupled to the conditioning circuit 124. As such, the conditioning circuit 124 is electrically coupled in between the coil loop 122 and the light generating unit 126.

The coil loop 122 is arranged to be inductively or magnetically coupled to the coil looped inductor 112. As such, the coil loop will induce a voltage or a potential difference across its terminals 123A and 123B in response to the pulsed EMF 130. The induced voltage will be an AC or alternating voltage corresponding to the pulsed EMF 130 and the current $I_1$ in the coil looped inductor 112. In particular, the induced voltage may comprise a sequence of damped or decaying sinusoidal oscillations, in correspondence with the shape of the pulsed EMF 130 and the current $I_1$.

The conditioning circuit 124 and the light generating unit 126 are coupled to the coil loop 122 such that a closed circuit is formed between the terminals 123A and 123B of the coil loop 122. As such, a current $I_2$ is induced through the coil loop 122 in response to the voltage induced across the terminals 123A and 123B.

The conditioning circuit 124 is configured to receive the current $I_2$ from the coil loop 122 and condition the current $I_2$. The conditioning circuit 124 conditions, alters and/or shapes the waveform of the current $I_2$. The conditioning circuit 124 then outputs a conditioned current $I_3$ to the light generating unit 126. The conditioned current $I_3$ has a shape and/or a waveform corresponding to a desired light output intensity of the light generating unit 126. The conditioned current $I_3$ may comprise at least a portion of the original current $I_2$. Conditioning a current (e.g. the current $I_2$ or otherwise) may be considered as altering, changing, and/or controlling the waveform of said current.

The light generating unit 126 is configured to receive the current $I_3$ from the conditioning circuit 124. The light generating unit 126 is further configured to emit light 140 in response to the current $I_3$. In particular, the light generating unit 126 is configured to emit light 140 that has an intensity that is generally proportional to the current $I_3$. It should be appreciated that different implementations of the light generating unit 126 may respond differently to the input current $I_3$. In some examples, the relationship between the light output of the light generating unit 126 and the input current $I_3$ may be substantially linear. In other examples, the relationship between the light output and the input current $I_3$ may be non-linear or curved.

The light generating unit 126 is arranged in the light therapy device 120 to provide the emitted light 140 to a part of the human or animal body. In some examples, the light generating unit 126 is arranged to provide the light 140 to the same part of the body to which the coil looped inductor 112 provides the pulsed EMF 130. In other examples, the light generating unit 126 is arranged to provide the light 140 to a different part of the body to which the coil looped inductor 112 provides the pulsed EMF 130.

Advantageously, the light therapy device 120 does not require a power supply in order to supply power to the light generating unit 126. Rather, the light generating unit 126 is able to emit light using electrical energy provided by the pulsed EMF device 110 via the pulsed EMF 130. Furthermore, with the present arrangement, the intensity of the emitted light 140 may be synchronised with the energy waveform of the pulsed EMF 130. This may have further advantages in that the effectiveness of the pulsed EMF therapy and the light therapy is enhanced.

In the illustrated examples, the coil loop 122 comprises one turn. However, in some examples, the coil loop 122 may comprise two or more turns. The number of turns may be a design choice based on the amount of power required by the light therapy device 120.

Optionally, the light generating unit 126 is configured to output infrared (IR) light. Alternatively, the light generating unit 126 may output red visible light. However, the light generating unit 126 may output light of any other wavelength or frequency at the designer's choice, depending on the type of physiological effect required. For example, the light generating unit 126 may output blue visible light, ultraviolet light, or any other wavelength of light between infrared and ultraviolet light.

Figure 2:
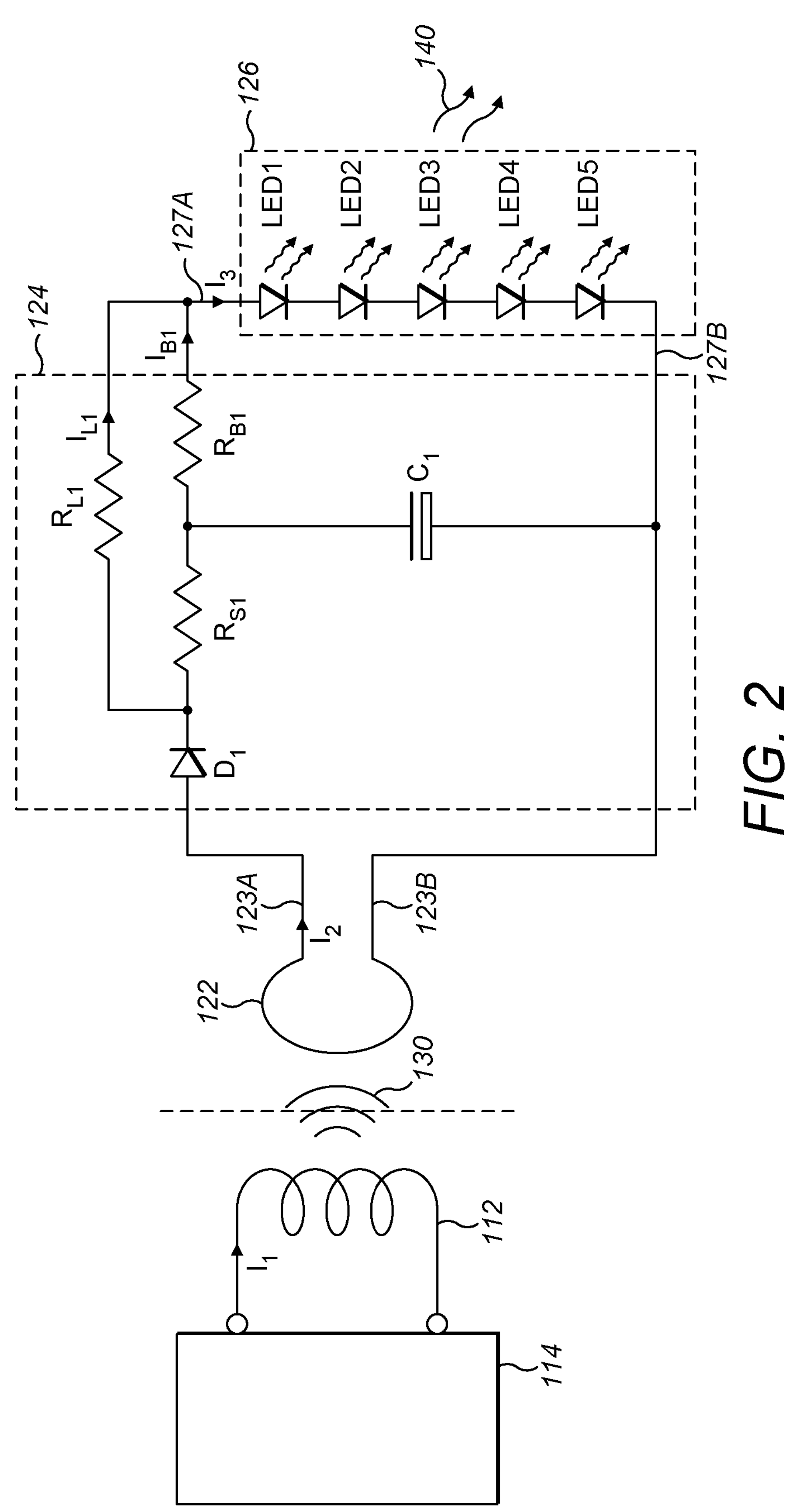
FIG. 2 shows a circuit level diagram of the system of FIG. 1.

FIG. 2 illustrates a more detailed circuit level view of the system 100. The conditioning circuit 124 comprises a diode $D_1$ and a capacitor $C_1$. The conditioning circuit 124 further comprises resistors $R_{S1}$, $R_{L1}$ and $R_{B1}$. The diode $D_1$ comprises an anode and a cathode. The anode of the diode $D_1$ is coupled to the first terminal 123A of the coil loop 122. The cathode of the diode $D_1$ is coupled to a first side of the resistor $R_{S1}$ and a first side of the resistor $R_{L1}$. A second side of the resistor $R_{S1}$ is coupled to a first side of the resistor $R_{B1}$. A second side of the resistor $R_{B1}$ is coupled to a first terminal 127A of the light generating unit 126. The first terminal 127A of the light generating unit 126 may be considered as a positive input terminal of the light generating unit 126. As such, the resistors $R_{S1}$ and $R_{B1}$ are arranged in series between the cathode of the diode $D_1$, and the first terminal 127A of the light generating unit 126. A first side of the capacitor $C_1$ is coupled to the second side of the resistor $R_{S1}$. A second side of the capacitor $C_1$ is coupled to the second terminal 123B of the coil loop 122 and a second terminal 127B of the light generating unit 126. The second terminal 127B of the light generating unit 126 may be considered as a negative input terminal of the light generating unit 126 As such, the capacitor $C_1$ is coupled between a common node between the resistors $R_{S1}$ and $R_{B1}$, and a common node between the second terminal 123B of the coil loop 122 and the second terminal 127B of the light generating unit 126. A second side of the resistor $R_{L1}$ is coupled to the first terminal 127A of the light generating unit 126. As such, the resistor $R_{L1}$ is arranged in series between the cathode of the diode $D_1$ and the first terminal 127A of the light generating unit. The resistor $R_{L1}$ is simultaneously in parallel with the series pair of resistors $R_{S1}$ and $R_{B1}$.

The diode $D_1$ is arranged to rectify the current $I_2$. In particular, the diode $D_1$ is configured to only pass a positive current from its anode to its cathode. As such, the diode D1 may be considered as a half-wave rectifier. Consequently, the current $I_2$ will only flow in a positive direction, e.g. clockwise around the light therapy device 120 from the first terminal 123A to the second terminal 123B.

Figure 5:
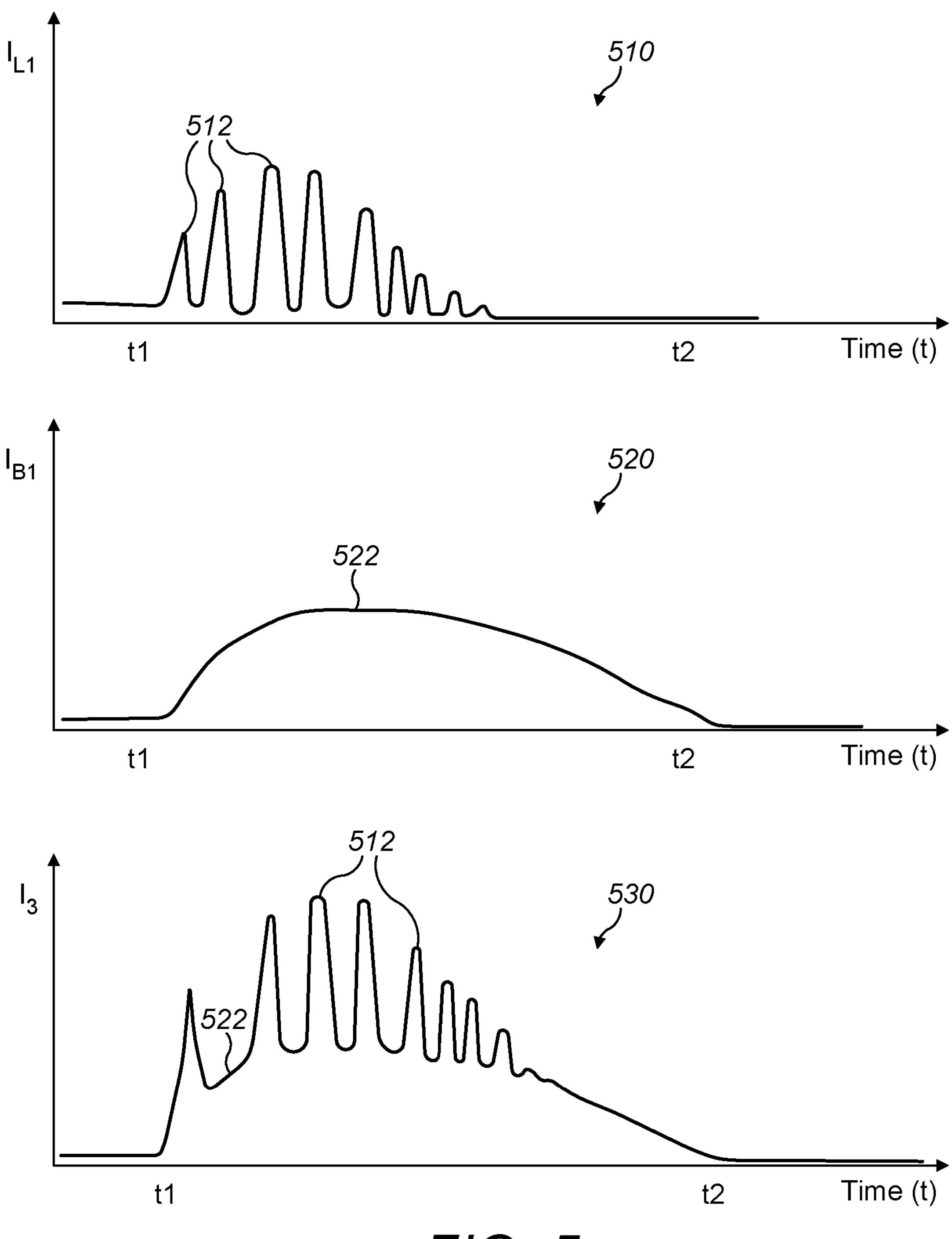
FIG. 5 shows various oscilloscope traces showing currents at various locations in the light therapy device of the system of FIG. 1, as a function of time.

The resistor $R_{L1}$ forms a resistive path between the rectifier $D_1$ and the input to the light generating unit 126. The resistive path receives a first portion of the current $I_2$ and attenuates said first portion. The amount of attenuation depends on the value of the resistor $R_{L1}$. The resistive path outputs the attenuated current $I_{L1}$. FIG. 5 illustrates an oscilloscope trace 510 showing the waveform of the attenuated current $I_{L1}$ between times $t_1$ and $t_2$. As shown, the current $I_{L1}$ resembles a half-wave rectified (and attenuated) version of the current $I_1$ shown in FIG. 4 between times t1 and t2. In particular, the current $I_{L1}$ comprises a sequence of peaks 512 that will be synchronised with and/or correspond to the positive peaks of the current $I_1$ shown in FIG. 4. The value of the resistor $R_{L1}$ can be selected to tune the overall amplitude of the peaks 512 of the current $I_{L1}$. For example, a larger resistance $R_{L1}$ will result in more attenuated (e.g. shorter) peaks 512, whereas a smaller resistance $R_{L1}$ will result in less attenuated (e.g. taller) peaks 512. However, the peaks 512 will still having an overall decaying shape as determined by the shape of the current $I_1$. The current path of the current $I_{L1}$ through the resistor $R_{L1}$ may be considered as a high frequency path. The current $I_{L1}$ may have a maximum peak value of 1 Amp, 10 Amps, 100 Amps, or any value within the range 1-100 Amps.

The resistors $R_{S1}$ and $R_{B1}$, and the capacitor $C_1$, together form a low-pass filter (LPF) between the rectifier $D_1$ and the light generating unit 126, and in parallel with the resistor $R_{L1}$. The LPF is configured to receive and filter a second portion of the current $I_2$, and output a filtered current $I_{B1}$. FIG. 5 further illustrates an oscilloscope trace 520 showing the waveform of the filtered current $I_{B1}$ between times $t_1$ and $t_2$. As shown, the current $I_{B1}$ resembles a half-wave rectified and subsequently smoothed version of the current $I_1$. In particular, the current $I_{B1}$ comprises a smooth pulse 522 that lasts over the duration of the current $I_1$ and the pulsed EMF 130 (e.g. between times $t_1$ and $t_2$). The values of the resistor $R_{S1}$ and capacitor $C_1$ may be selected so that the low pass filter has an appropriate cut-off frequency to provide the smooth pulse 522. Furthermore, the value of the resistor $R_{B1}$ may be selected to control the overall current generated by the LPF. In particular, $R_{B1}$ may control overall amplitude of the smooth pulse 522. For example, a larger resistor $R_{B1}$ may result in the smooth pulse 522 having a more attenuated (e.g. smaller) amplitude. A smaller resistor $R_{B1}$ may result in the smooth pulse 522 having a less attenuated (e.g. larger) amplitude. The current path of the current $I_{B1}$ through the resistors $R_{S1}$ and $R_{B1}$ may be considered as a low frequency path. The smooth pulse 522 of the current $I_{B1}$ may have a maximum peak value of 10 Amps, or any value within the range 0-10 Amps. Furthermore, the smooth pulse of the current $I_{B1}$ may have a duration of 1 millisecond, 2 milliseconds, or any amount of time within the range 1-2 milliseconds.

The components $R_{S1}$, $R_{L1}$, $R_{B1}$ and $C_1$ may be considered together as an interface circuit comprising the resistive path and the low-pass filter described above.

Reference is now made back to FIG. 2. Since the resistors $R_{L1}$ and $R_{B1}$ are coupled to the same terminal 127A, the currents $I_{L1}$ and $I_{B1}$ will be summed or superimposed to form the current $I_3$. The current $I_3$ is then supplied to the light generating unit 126 as described above. FIG. 5 illustrates an oscilloscope trace 530 showing the waveform of the current $I_3$. As shown, the current $I_3$ comprises the sequence of peaks 512 synchronised with or corresponding to the positive peaks of the current $I_1$ (and correspondingly the positive energy peaks of the pulsed EMF 130). The current $I_3$ also comprises the smooth pulse 522 over the duration of the current $I_1$ and the EMF pulse. Due to the current path provided by the capacitor C1, the current $I_3$ may comprise some but not all of the current $I_2$. The current $I_3$ may have a maximum peak value of 1 Amps, 10 Amps, 100 Amps, or any other value within the range 1-100 Amps.

Referring to FIG. 2, the light generating unit 126 comprises a plurality of light-emitting diodes (LEDs). The light generating unit 126 comprises five LEDs LED1, LED2, LED3, LED4, and LED5. The LEDs LED1-LED5 are arranged in series between the first (e.g. positive) input terminal 127A and the second (e.g. negative) input terminal 127B of the light generating unit 126. In particular, an anode of the LED1 is coupled to the first input terminal 127A. An anode of the LED2 is coupled to a cathode of the LED1. An anode of the LED3 is coupled to a cathode of the LED2. An anode of the LED4 is coupled to a cathode of the LED3. An anode of the LED5 is coupled to a cathode of the LED4. A cathode of the LED5 is coupled to the second input terminal 127B. The second input terminal 127B is coupled to the second terminal 123B of the coil loop 122.

Each LED LED1-LED5 is configured to emit light in response to the current $I_3$. In particular, each LED1-LED5 emits light that has an intensity that is generally proportional to the current level $I_3$. In some examples, the relationship between the light output of the LEDs and the input current $I_3$ may be substantially linear. In other examples however, the relationship between the light output and the input current $I_3$ may be non-linear or curved. The precise current-response relationship between the light output and the current $I_3$ may depend on the characteristics of the LEDs. The light outputs of the LEDs LED1-LED5 combine to form the light 140 emitted by the light generating unit 126. For example, the LEDs LED1-LED5 may be arranged in an array to provide the combined light output 140. The LEDs are arranged to be placed adjacent to, near or around a part of the body (e.g. a limb or joint).

Figure 6:
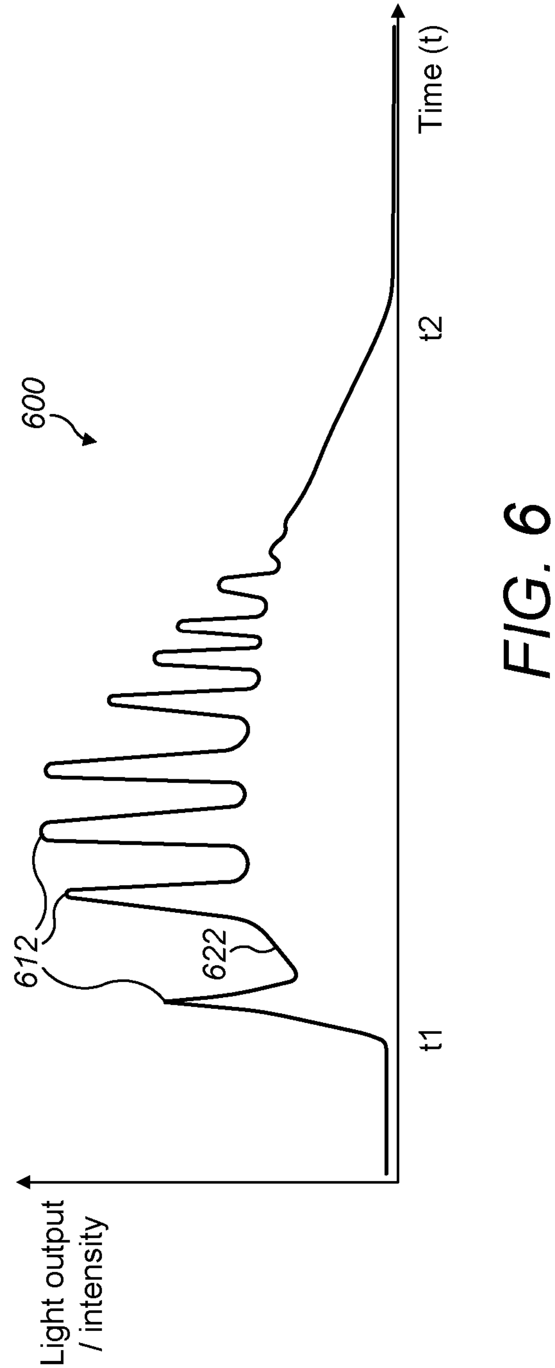
FIG. 6 shows the intensity of light emitted by the light therapy device of the system of FIG. 1, as a function of time.

FIG. 6 illustrates the intensity of the emitted light 140 as a function of time between the times t1 and t2. As shown, the emitted light comprises a light pulse 600 between the times t1 and t2. The light pulse 600 has an intensity that is proportional to the current $I_3$. In particular, the light pulse 600 comprises a sequence of decaying peaks 612. The sequence of decaying peaks 612 are synchronised with or correspond with the peaks 512 of the current $I_3$. Consequently, the peaks 612 are synchronised with or correspond with the positive peaks of the current $I_1$ in the inductor 112, and the positive peaks of the EMF pulse 130. The light pulse 600 further comprises a low-frequency pulse 622. The low frequency pulse 622 lasts over the duration of the light pulse 600 between times t1 and t2. The low-frequency pulse 622 corresponds with the low-frequency pulse 522 of the current $I_3$ shown in FIG. 5. As will be appreciated, values of the components $R_{S1}$, $R_{B1}$, $R_{L1}$ and $C_1$ can be chosen to shape the current $I_3$, and consequently control the intensity of the light that is outputted by the LEDs in response to the EMF pulse 130. The component of the light pulse 600 corresponding to the sequence of peaks 612 (i.e. the high frequency component of the light pulse 600) may have a maximum peak intensity of 10 W/cm$^2$, 100 W/cm$^2$, or any value between 10-100 W/cm$^2$. The low frequency pulse 622 of the light pulse 600 (i.e. the low frequency component of the light pulse 600) may have a peak intensity of 10 mW/cm$^2$, 1000 mW/cm$^2$, or any value between 10-1000 mW/cm$^2$. The low frequency pulse 622 may have a duration of 1 millisecond, 2 milliseconds, or for any amount of time between 1-2 milliseconds. Over time, the light generating unit may output a plurality of light pulses 600. In one example, over a period of 30 minutes, the light generating unit may output a total light energy of 1 J/cm$^2$, 10 J/cm$^2$ or any value between 1-10 J/cm$^2$.

Advantageously, synchronising the peaks 612 of the light pulse 600 with the peaks of the EMF pulse 130 has been found to provide an overall enhanced physiological effect on the human or animal body. Thus, the synchronisation may result in enhanced pulsed EMF therapy and light therapy. Furthermore, the low-frequency pulse 622 means that the light pulse 600 is observed by a human as a single "blink" over the duration of the light pulse 600. Therefore, the low frequency pulse 622 may protect the human eyes from the higher intensity peaks 612 of light. Otherwise, an observer might only observe high intensity flashes of light caused by the high intensity peaks 612, which may cause damage to the observer's eyes.

In the illustrated example of FIG. 2, the light generating unit 126 comprises five LEDs LED1, LED2, LED3, LED4, and LED5. However, in other examples, the light generating unit 126 may comprise any number of LEDs. For example, the light generating unit 126 may comprise one or more LEDs. Where the light generating unit 126 comprises one LED, the LED may be arranged with its anode coupled to the first input terminal 127A and its cathode coupled to the second input terminal 127B.

Figure 3:
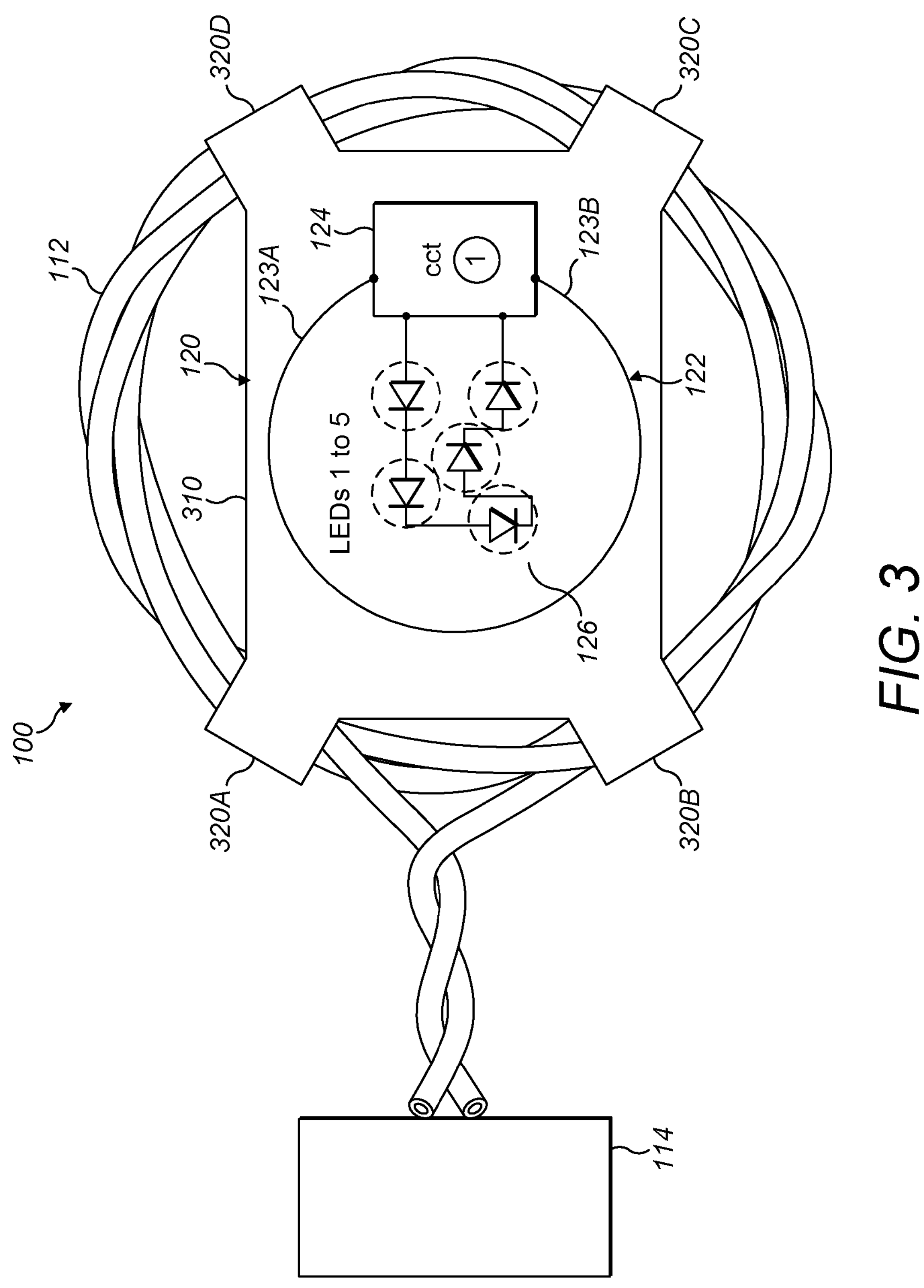
FIG. 3 shows a structural view of the system of FIG. 1.

FIG. 3 shows a structural view of the system 100. The system 100 comprises a housing 310. The housing 310 contains or encloses the light therapy device 120. In particular, the circuitry of the light therapy device 120, including the coil loop 122, conditioning circuit 124 and light generating unit 126, are contained in the housing 310. The housing 310 may be shaped and/or dimensioned to be a similar size to the coil looped inductor 112 of the pulsed EMF device 110. For example, the housing may have a length that is the same or less than a diameter of the coil looped inductor 112, and a width that is the same or less than the diameter of the coil looped inductor 112.

The housing 310 comprises a plurality of clips 320A, 320B, 320C and 320D. The clips 320A, 320B, 320C and 320D are configured to secure or attach the housing 310 to the coil looped inductor 112.

FIG. 3 also indicates an example arrangement of the coil loop 122, conditioning circuit 124 and the light generating unit 126 within the housing 310. The coil loop 122 may be arranged within the housing 310 such that the coil loop 122 is in close proximity to the coil looped inductor 112 when the housing 310 is attached to the coil looped inductor 122. In particular, the coil loop 122 may be arranged such that the coil loop 122 is inductively or magnetically coupled with the coil looped inductor 112. Optionally, as shown in FIG. 3, the coil loop 122 is arranged in the housing 310 so that it shares the same axis as the coil looped inductor 112 when the housing is attached to the coil looped inductor 112. Advantageously, this has been found to improve the inductive coupling between the coil looped inductor 112 and the coil loop 122 and the efficiency of energy transfer between the coil looped inductor 112 and the coil loop 122. However, in other examples, the coil loop 122 may not necessarily share the same axis as the coil looped inductor 112. For example, the coil loop 122 may be arranged to have an axis that is different to the axis of the coil looped inductor 112. In some examples, the coil loop 122 may be arranged to have an axis that is different to but in parallel with the axis of the coil looped inductor 112.

The light generating unit 126 may be arranged in the housing 310 such that the light generating unit 126 emits light 140 to the same body part to which the coil looped inductor emits the pulsed EMF 130. For example, the light generating unit 126 may be arranged in the housing 310 to emit light 140 along the axis of the coil looped inductor 112. Optionally, as shown in FIG. 3, the light generating unit 126 is arranged in the centre of the coil loop 122. Advantageously, by providing the pulsed EMF 130 and the light 140 to the same body part, the pulsed EMF 130 and the light 140 may work together to provide an enhanced physiological effect on the body.

In some examples, the system 100 is contained in a further housing (not shown in FIG. 3). In particular, both the housing 310 and the pulsed EMF device (e.g. the circuitry 114 and the coil looped inductor 112), may be contained in the same common housing. Advantageously, the system 100 may be provided as a single, compact device that is capable of providing both pulsed EMF therapy and light therapy.

In other examples, the system 100 may not be entirely contained in a single housing. Instead, the pulsed EMF device 110 may be contained in a separate housing (not shown) without the light therapy device 120. The housing 310 containing the light therapy device 120 may be configured to attach to the housing containing the pulsed EMF device 110 such that the coil loop 122 is inductively coupled with the coil looped inductor 112 and the light therapy device 120 operates as described above. As such, in this example, the system 100 may be provided as a modular system comprising a pulsed EMF device with a detachable light therapy device 120. Advantageously, a user can choose whether or not to use the light therapy device 120 in combination with the pulsed EMF device 110.

In another example, some of the pulsed EMF device 110 may be comprised in a separate housing (not shown). In particular, the circuitry 114 and other parts of the pulsed EMF device 110 may be comprised in the separate housing, but the coil loop inductor 112 may protrude from, extend from or otherwise be external to the separate housing. As such, the coil looped inductor 112 may be exposed. It will be appreciated that the coil looped inductor 112 can be suitably insulated such that it is safe to touch and operate the pulsed EMF device 110. The housing 310 containing the light therapy device 120 may be configured to attach to the coil looped inductor 112 as is described above, for example with the clips 320A, 320B, 320C and 320D. Advantageously, the system 100 can be provided as a modular system.

As shown in FIG. 3 and described above, the housing 310 containing the light therapy device 120 can attach to the coil looped inductor 112 of the pulsed EMF device 110. When attached, the coil loop 122 is inductively or magnetically coupled with the coil looped inductor 112 and therefore the light therapy device 120 can harvest and use power from the EMF pulses emitted by the coil looped inductor 112 in order to emit light. When the coil looped inductor 112 is positioned close to a body part, said body part can benefit from the combined physiological effect of the emitted light and EMF pulses.

Figure 14:
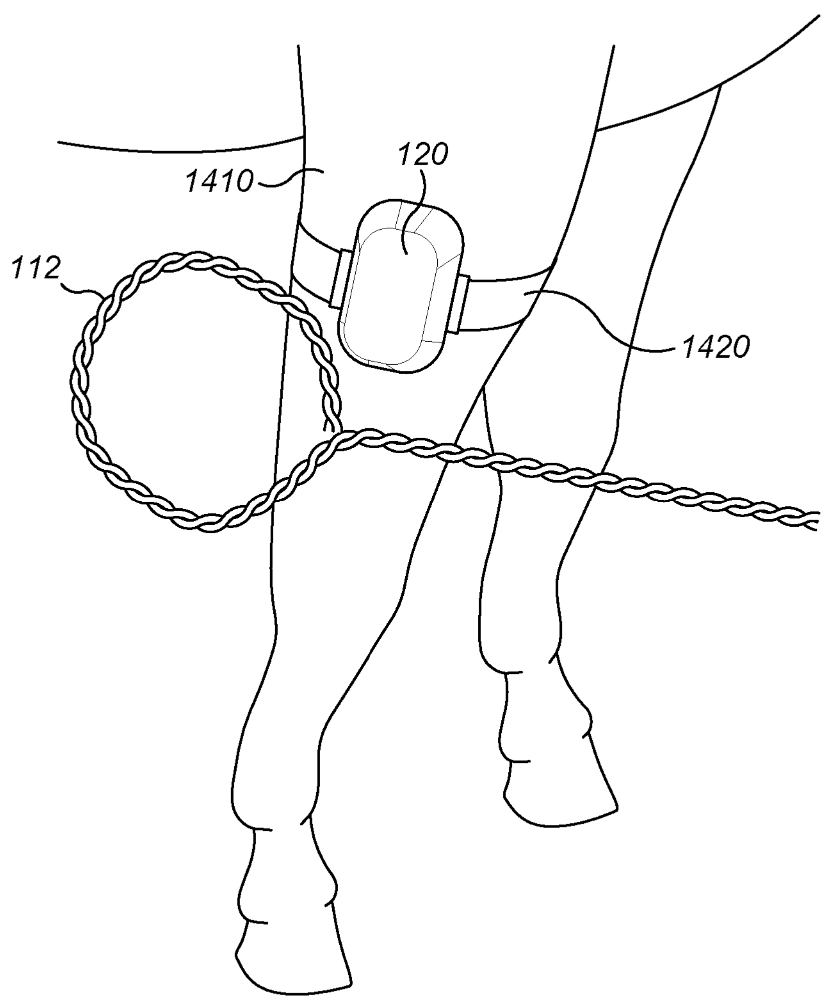
FIG. 14 shows an example way of using a system comprising a pulsed electromagnetic field therapy device and a light therapy device.

FIG. 14 shows an alternative way of using the system 100. In particular, FIG. 14 shows an alternative way in which the light therapy device 120 can be used in combination with the pulsed EMF device 110. The light therapy device 120 can be attached to or otherwise secured to a human or animal body part that is to undergo light treatment. The example of FIG. 14 shows the light therapy device 120 attached to a leg 1410 of a horse. The light therapy device 120 can include means for attaching the light therapy device 120 to the leg 1410. For example as shown, the light therapy device 120 can include a strap 1420. In use, the coil looped inductor 112 is positioned close to and moved over the leg 1410 to provide pulsed EMF treatment to the leg 1410. When the coil looped inductor 112 is in the proximity of the light therapy device 120 the light therapy device 120 will be powered by the EMF pulses emitted by the coil looped inductor 112, as already described above. In particular, the coil loop 122 in the light therapy device 120 induces a current in response to the EMF pulses. The LEDs in the light therapy device 120 will receive at least some of the induced current and emit light pulses to provide light treatment to the leg 1410 as already described. Moreover, the leg 1410 will benefit from the combined physiological effects of the emitted light and the EMF pulses. In such examples, the light therapy device 120 is used as a wearable device that is physically separate to the pulsed EMF device 110, instead of as a modular attachment of the pulsed EMF device 110 as shown in FIG. 3. Optionally the LEDs are located on the underside of the light therapy device 120 between the device 120 and the leg 1410, in order to provide the light pulses to the leg 1410. It will be appreciated that the light therapy device 120 can be secured or attached to any other human or animal body parts in a similar way.

The amount of power transferred between the coil looped inductor 112 and the coil loop 122 depends on the orientation of the coil looped inductor 112 relative to the coil loop 122. Power transfer between the coil looped inductor 112 and the coil loop 122 is maximal when both loops 112 and 122 lie in parallel planes and share the same axis. This may be considered as the optimal alignment or orientation between the loops 112 and 122. The power transfer is further increased when the loops 112 and 120 are as close as possible to one another. However, when the light therapy device 120 is used as a wearable device, optimal power transfer between the loops 112 and 122 may be inconsistent during use. For example, the user may not consistently provide the coil looped inductor 112 in the correct alignment or orientation with respect to the coil loop 122 when the coil looped inductor 112 is positioned over the light therapy device 120. More particular, the user may not provide the coil looped inductor 112 in a plane that is parallel to the plane of the coil loop 122. Rather, through user error, the coil looped inductor 112 may be provided in a plane that is angled relative to the plane of the coil loop 122. Consequently, the axes of the loops 112 and 122 are also misaligned. This can result in intermittent or inconsistent power transfer to the light therapy device 120, and lead to ineffective light therapy treatment from the device 120.

As described in more detail below, in some examples the light therapy device can include at least two coil loops. The coil loops can be arranged in different planes. In particular, the coil loops can be arranged in different planes that intersect at angles to one another. Optionally, the different planes are orthogonal, or at about 90 degrees, to one another. Consequently, the power transfer between the coil looped inductor 112 and the light therapy device can be made independent of the angle of the coil looped inductor relative to the light therapy device. Advantageously, this angular independence enables consistent and maximal power transfer from the coil looped inductor 112 to the light therapy device, independent of the orientation of the coil looped inductor 112.

Figure 15:
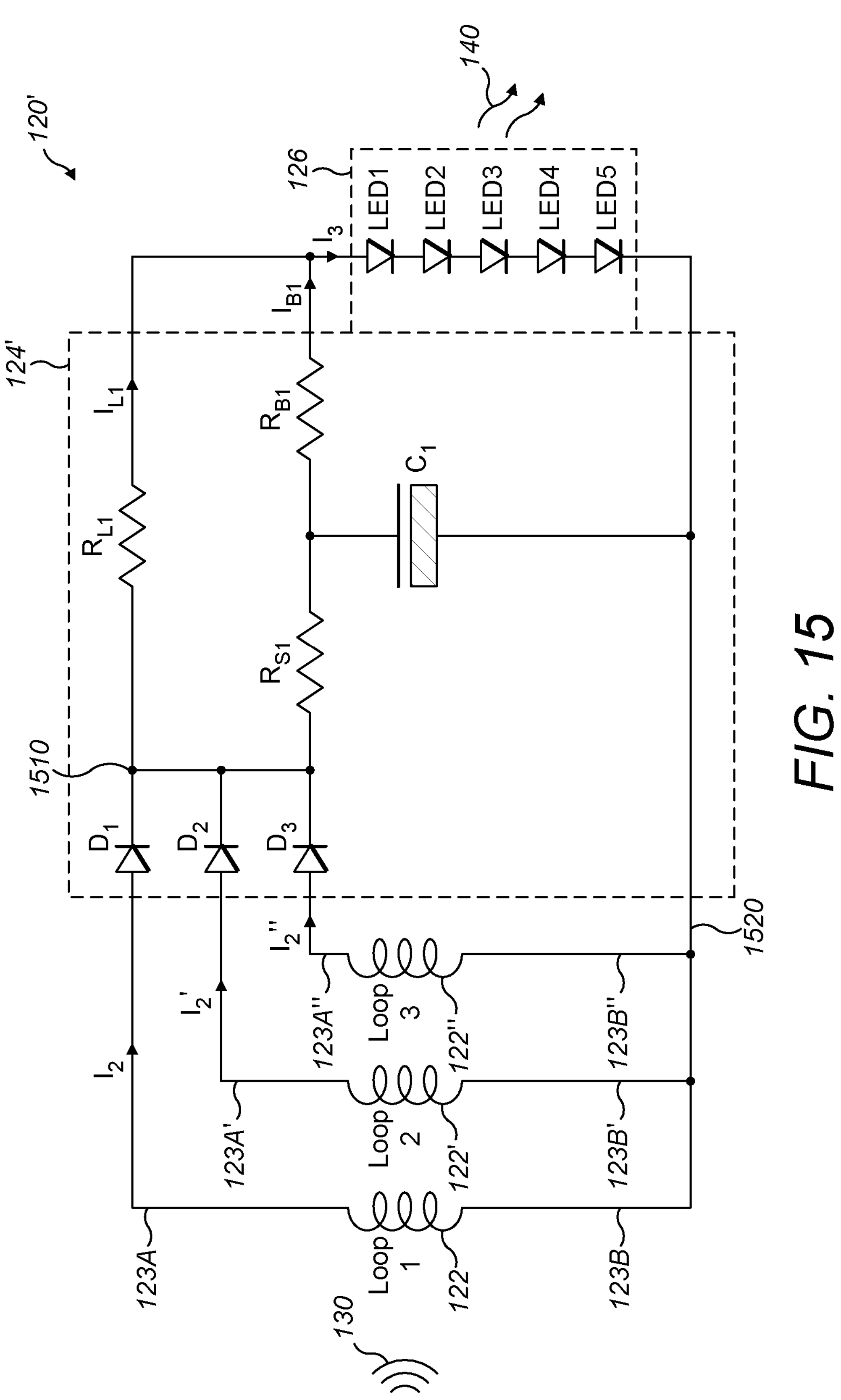
FIG. 15 shows a light therapy device according to another example of the present disclosure.

FIG. 15 shows a circuit schematic of a light therapy device 120' which achieves the above-described angular independence. The light therapy device 120' corresponds to the light therapy device 120 described previously, but with the following differences. The light therapy device 120' further includes a second coil loop 122'. The second coil loop 122' has a first terminal 123A' and a second terminal 123B'. The conditioning circuit 124' is electrically coupled to the second coil loop 122'. In particular, the conditioning circuit 124' is electrically coupled to the terminals 123A', 123B' of the second coil loop 122'. As such, the conditioning circuit 124' is electrically coupled in between the second coil loop 122' and the light generating unit 126 as well as in between the first coil loop 122 and the light generating unit 126. Moreover, the second terminal 123B' of the second coil loop 122' is coupled to the second terminal 123B of the first coil loop 122 at a common node 1520.

The conditioning circuit 124' of the light therapy device 120' further includes a second diode D2. The second diode D2 acts as a rectifier for current generated/induced in the second coil loop 122', similarly to how the diode D1 acts as a rectifier for the current generated/induced in the first coil loop 122. An anode of the diode D2 is coupled to the first terminal 123A' of the second coil loop 122'. A cathode of the diode D2 is coupled to the cathode of the diode D1 at a common node 1510. As such, the cathode of the diode D2 is also coupled to first side of the resistor $R_{S1}$ and the first side of the resistor $R_{L1}$.

The first coil loop 122 and the rectifier D1 are coupled in series between the common nodes 1510 and 1520. The second coil loop 122' and the rectifier D2 are coupled in series between the common nodes 1510 and 1520. Therefore, the series combination of the first coil loop 122 and the rectifier D1 is coupled in parallel with the series combination of the second coil loop 122' and the rectifier D2.

Figure 16:
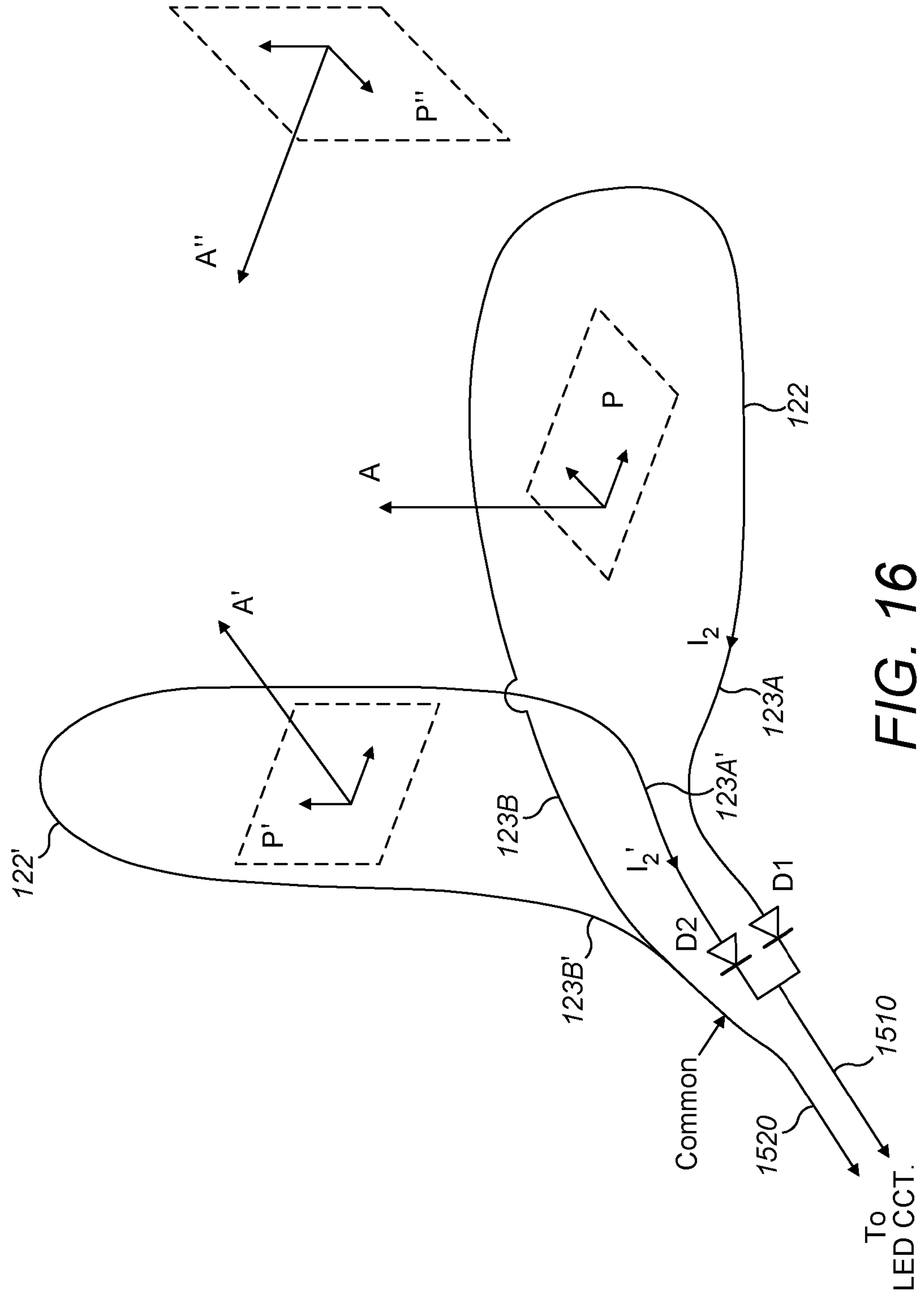
FIG. 16 illustrates an example arrangement of the coil loops of the light therapy device of FIG. 15.

Reference is made to FIG. 16, which shows a perspective view of the coil loops 122 and 122' of the light therapy device 120'. As shown, the first coil loop 122 is arranged in a first plane P. The first coil loop 122 also has an axis A which is also a normal vector to the first plane P. Furthermore, the second coil loop 122' is arranged in a second plane P' that is different to the first plane P. Although not shown, the first plane P and the second plane P' will intersect at an angle. As such, the planes P and P' are not parallel to one another. The second coil loop 122' also has an axis A' which is also a normal vector to the second plane P'. Optionally, the coil loops 122 and 122' are arranged such that their respective planes P and P' are substantially orthogonal or perpendicular. However, it will be appreciated that non-perpendicular or non-orthogonal angles between the planes P and P' can be used. For example, the angle between the planes can be 45 degrees to 90 degrees.

The operation of the light therapy device 122' is described as follows. The light therapy device 122' can be used as a wearable device by securing or attaching it to an animal or human body part (e.g. as shown in FIG. 14 and described above). In use, a user may provide the coil looped inductor 112 over the light therapy device 120'.

In a first scenario, the coil looped inductor 112 is aligned with the first coil loop 122. In particular, the coil loop inductor 112 is orientated in a plane that is parallel to the first plane P. The coil loop inductor 112 is also provided so that the axis of the coil loop inductor 112 is substantially aligned with the axis A. In this scenario, the EMF pulse 130 induces a current $I_2$ in the first coil loop 122, which powers the light therapy device 120' as already described with respect to the light therapy device 120. In particular, the current $I_2$ is received by the conditioning circuit 124'. The conditioning circuit 124' conditions, alters and/or shapes the waveform of the current $I_2$ and outputs a conditioned current $I_3$. The conditioned current $I_3$ is then supplied to the light generating unit 126. The conditioning circuit 124' and the light generating unit 126 function as has already described above for the light therapy device 120, and therefore the functionality of the components D1, $R_{S1}$, $R_{L1}$, $R_{B1}$, $C_1$ and LED1-LED5 are not described in detail. Due to the alignment of the coil looped inductor 112, the second coil loop 122' may not induce a sufficient current to contribute to the powering of the light therapy device 120'. However, the coil looped inductor 112 is optimally aligned with the first coil loop 122 and therefore maximal power transfer is achieved in this orientation.

In a second scenario, the coil looped inductor 112 is aligned with the second coil loop 122'. In particular, the coil looped inductor 112 is orientated in a plane that is parallel to the second plane P'. The coil looped inductor 112 is also provided so that the axis of the coil loop inductor 112 is substantially aligned with the axis A'. In this scenario, the EMF pulse 130 induces a current $I_2'$ in the second coil loop 122'. However, due to the alignment of the coil looped inductor 112, the first coil loop 122 may not induce a sufficient current to contribute to the powering of the light therapy device 120'. Instead, the current $I_2'$ powers the light therapy device 120' similarly to how the current $I_2$ would power the light therapy device 120' in the first scenario above. In particular, the current $I_2'$ is received by the conditioning circuit 124'. The conditioning circuit 124' conditions, alters and/or shapes the waveform of the current $I_2'$ similarly to how the conditioning circuit 124' would condition the current $I_2$. In particular, the diode D2 rectifies the current $I_2'$ similarly to how the diode D1 would rectify the current $I_2$. The components $R_{S1}$, $R_{L1}$, $R_{B1}$, $C_1$ (i.e. the interface circuit) further conditions the current $I_2'$ as already described in respect of the current $I_2$. The conditioning circuit 124' outputs a conditioned current $I_3$. The conditioned current $I_3$ is then supplied to the light generating unit 126. The light generating unit 126 then emits light as already described above. In this scenario, the coil looped inductor 112 is optimally aligned with the second coil loop 122' and therefore maximal power transfer is also achieved in this orientation.

In a third scenario, the coil looped inductor 112 is angled relative to both coil loops 122 and 122'. In particular, the coil looped inductor 112 is orientated in a plane that is angled relative to both of the planes P and P'. A current $I_2$ will be induced in the coil loop 122 and a current $I_2'$ will also be induced in the coil loop 122'. The diode D1 will rectify the current $I_2$. The diode D2 will rectify the current $I_2'$. The rectified currents $I_2$ and $I_2'$ will then be summed at the common node 1510. The summed current $I_2+I_2'$ is supplied to the input of the interface circuit ($R_{S1}$, $R_{L1}$, $R_{B1}$, $C_1$). The interface circuit further conditions the summed current $I_2+I_2'$ as already described above for the current $I_2$. The conditioning circuit 124' outputs a conditioned current $I_3$. The conditioned current 13 is then supplied to the light generating unit 126. The light generating unit 126 then emits light as already described above.

In the third scenario, the coil looped inductor 112 is not optimally aligned with either coil loop 122 and 122'. However, weaker currents $I_2$ and $I_2'$ are still induced in both coil loops 122 and 122'. The sum of the currents is provided to the rest of the circuit via the common node 1510. Advantageously, this enables the light therapy device 120' to achieve maximal power transfer even when the coil looped inductor 112 is not optimally aligned with the light therapy device 120'. In particular, the light therapy device 120' is able to achieve more optimal power transfer, independent of the angle between the coil looped inductor 112 and the light therapy device 120'. As such, this reduces the risk of inefficient or intermittent power transfer to the light therapy device 120' during use. Moreover, this improves the effectiveness of the light therapy provided by the light therapy device 120', especially when the light therapy device 120' is used as a wearable device.

Figure 17:
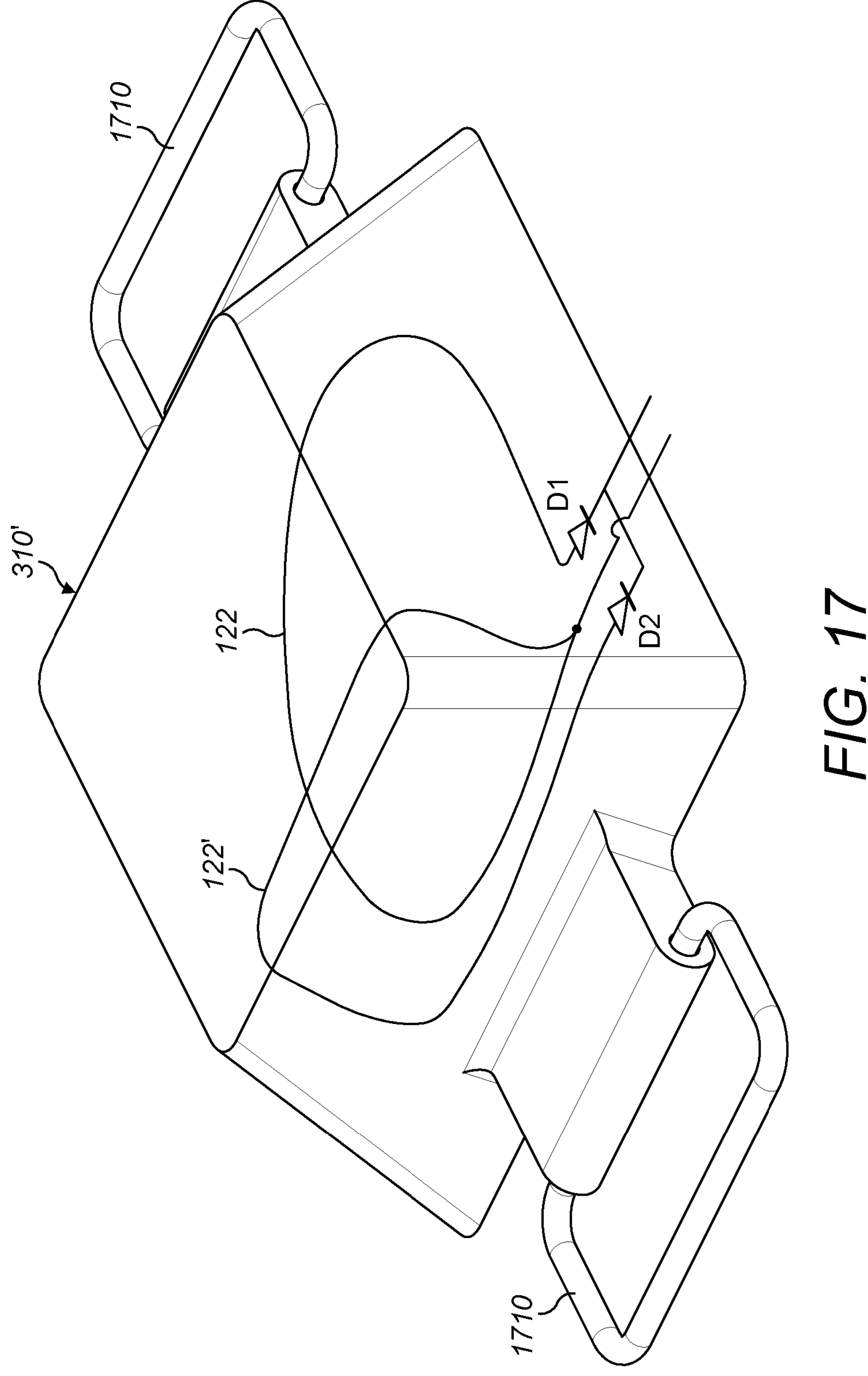
FIG. 17 shows a structural view of the light therapy device of FIG. 15.

FIG. 17 shows an example arrangement of the light therapy device 120' within a housing 310'. In particular, the arrangement of the coil loops 122 and 122' within the housing 310' is illustrated. As shown, the housing 310' is shaped or otherwise structured to accommodate the coil loops 122 and 122' in the arrangements described above. Furthermore, the housing 310' includes a means 1710 for securing the housing 310' to an animal or human body part. In the illustrated example, the means 1710 are buckles for attaching a strap or band which can be looped around the body part. However, it will be appreciated that the housing 310' can include any other means for attaching or securing the housing 310' to a body part. Although not shown, the housing 310' can accommodate the remaining components and circuitry of the light therapy device 120'.

It has been found that the two coil loops 122 and 122' are sufficient to observe the improvements in power transfer described above. However, to provide further enhanced angular independence, a third coil loop can optionally be included. The optional third coil loop 122" is shown in FIG. 15. The third coil loop 122" has a first terminal 123A" and a second terminal 123B". The conditioning circuit 124' is electrically coupled to the third coil loop 122". In particular, the conditioning circuit 124' is electrically coupled to the terminals 123A", 123B" of the third coil loop 122'. As such, the conditioning circuit 124' is further electrically coupled in between the third coil loop 122" and the light generating unit 126. Moreover, the second terminal 123B" of the third coil loop 122" is coupled to the second terminal 123B of the first coil loop 122 and the second terminal 123B' of the second coil loop 122' at the common node 1520. The conditioning circuit 124' of the light therapy device 120' further includes a third diode D3. The third diode D3 acts as a rectifier for current generated/induced in the third coil loop 122", similarly to how the diode D1 acts as a rectifier for the current generated/induced in the first coil loop 122. An anode of the diode D3 is coupled to the first terminal 123A" of the third coil loop 122". A cathode of the diode D3 is coupled to the cathode of the diode D2 and the cathode of the diode D1 at the common node 1510. As such, the cathode of the diode D3 is also coupled to first side of the resistor $R_{S1}$ and the first side of the resistor $R_{L1}$.

The third coil loop 122" and the rectifier D3 are coupled in series between the common nodes 1510 and 1520. Therefore, the series combination of the third coil loop 122" and the rectifier D3 is coupled in parallel with the series combination of the first coil loop 122 and the rectifier D1, and the series combination of the second coil loop 122' and the rectifier D2.

With reference to FIG. 16, the third coil loop 122" can be arranged in a third plane P" that is different to the first plane P and to the second plane P'. Although not shown, the third plane P" will intersect with both the first plane P and the second plane P' at angles. As such, the plane P" is not parallel with either planes P and P'. The third coil loop 122" may have an axis A" which is also a normal vector to the third plane P". Optionally, the coil loop 122" is arranged such that its plane P" is substantially orthogonal perpendicular to both the first plane P and the second plane P'. In particular, the plane P" is substantially orthogonal to the plane P'. Simultaneously, the plane P" is also substantially orthogonal to the plane P. However, it will be appreciated that non-perpendicular or non-orthogonal angles between the plane P" and the planes P and P' can be used. For example, the angle between the plane P" and the plane P can be 45 degrees to 90 degrees. Furthermore, the angle between the plane P" and the plane P' can be 45 degrees to 90 degrees.

In a further scenario during use of the system 100, the coil looped inductor 112 can be aligned with the third coil loop 122". In particular, the coil looped inductor 112 is orientated in a plane that is parallel to the third plane P". The coil looped inductor 112 is also provided so that the axis of the coil loop inductor 112 is substantially aligned with the axis A". In this scenario, the EMF pulse 130 induces a current $I_2"$ in the third coil loop 122". However, due to the alignment of the coil looped inductor 112, the first coil loop 122 and the second coil loop 122' may not induce sufficient currents to contribute to the powering of the light therapy device 120'. Instead, the current $I_2''$ powers the light therapy device 120' similarly to how the current $I_2$ or $I_2'$ would power the light therapy device 120' in the scenarios previously described above. In particular, the current $I_2''$ is received by the conditioning circuit 124'. The conditioning circuit 124' conditions, alters and/or shapes the waveform of the current $I_2''$ similarly to how the conditioning circuit 124' would condition the current $I_2$ or $I_2'$. In particular, the diode D3 rectifies the current $I_2''$ similarly to how the diode D1 would rectify the current $I_2$. The components $R_{S1}$, $R_{L1}$, $R_{B1}$, $C_1$ (i.e. the interface circuit) further conditions the current $I_2''$ as already described in respect of the current $I_2$. The conditioning circuit 124' outputs a conditioned current $I_3$. The conditioned current $I_3$ is then supplied to the light generating unit 126. The light generating unit 126 then emits light as already described above. In this scenario, the coil looped inductor 112 is optimally aligned with the third coil loop 122" and therefore maximal power transfer is also achieved in this orientation.

In another scenario during use of the system 100, the coil looped inductor 112 is angled relative to all of the coil loops 122, 122' and 122". In particular, the coil looped inductor 112 is orientated in a plane that is angled relative to each of the planes P, P' and P". A current $I_2$ will be induced in the coil loop 122, a current $I_2'$ will be induced in the coil loop 122', and a current $I_2''$ will also be induced in the coil loop 122". The diode D1 will rectify the current $I_2$. The diode D2 will rectify the current $I_2'$. The diode D3 will rectify the current $I_2''$. The rectified currents $I_2$, $I_2'$ and $I_2''$ will then be summed at the common node 1510. The summed current $I_2+I_2'+I_2''$ is supplied to the input of the interface circuit ($R_{S1}$, $R_{L1}$, $R_{B1}$, $C_1$). The interface circuit further conditions the summed current $I_2+I_2'+I_2''$ as already described above for the current $I_2$. The conditioning circuit 124' outputs a conditioned current $I_3$. The conditioned current $I_3$ is then supplied to the light generating unit 126. The light generating unit 126 then emits light as already described above.

In the third scenario, the coil looped inductor 112 is not optimally aligned with either coil loops 122, 122' or 122". However, weaker currents $I_2$, $I_2'$ and $I_2''$ are still induced in the respective coil loops 122, 122' and 122". The sum of the currents is provided to the rest of the circuit via the common node 1510. Advantageously, this enables the light therapy device 120' to achieve further improved power transfer even when the coil looped inductor 112 is not optimally aligned with the light therapy device 120'. In particular, the light therapy device 120' is able to achieve more optimal power transfer, independent of the angle between the coil looped inductor 112 and the light therapy device 120'. As such, this further reduces the risk of inefficient or intermittent power transfer to the light therapy device 120' during use. Moreover, this further improves the effectiveness of the light therapy provided by the light therapy device 120', especially when the light therapy device 120' is used as a wearable device.

In the illustrated examples, each coil loop 122, 122' and 122" comprises one turn. However, in some examples, each coil loop 122, 122' and 122" may comprise two or more turns. The number of turns may be a design choice based on the amount of power required by the light therapy device 120'. Optionally, each coil loop 122, 122' and 122" has the same number of turns. Alternatively, the coil loops can have different numbers of turns. With reference to FIG. 17, in one example, the first coil loop 122 can have one turn. Although not shown, the second coil loop 122' can have any different number of turns, e.g. two, three, four or more turns. If the second coil loop 122' has more turns, the second coil loop 122' can be reduced in height or width in comparison to the first coil loop 122, whilst achieving a similar inductance characteristic to the first coil loop 122. This may enable the coil loops 122 and 122' to better fit into the housing 310'. For example, the vertically positioned second coil loop 122' can be made to have more than one turn. This will allow the height of the coil loop 122' to be reduced without significantly impacting its inductance, so that the coil loop 122' can better fit into a housing 310' that has limited height. In one example, the coil loop 122 can have one turn. The coil loop 122' can have four turns, but have a quarter of the height of the coil loop 122.

The system 100 described above combines a pulsed EMF therapy device 110 and a light therapy device 120, whereby the light therapy device 120 is powered by the pulsed EMF 130 emitted by the pulsed EMF device 110 without the need for a separate power supply. Similar principles to those described above may be used to power alternative devices to the light therapy device 120.

Figure 7:
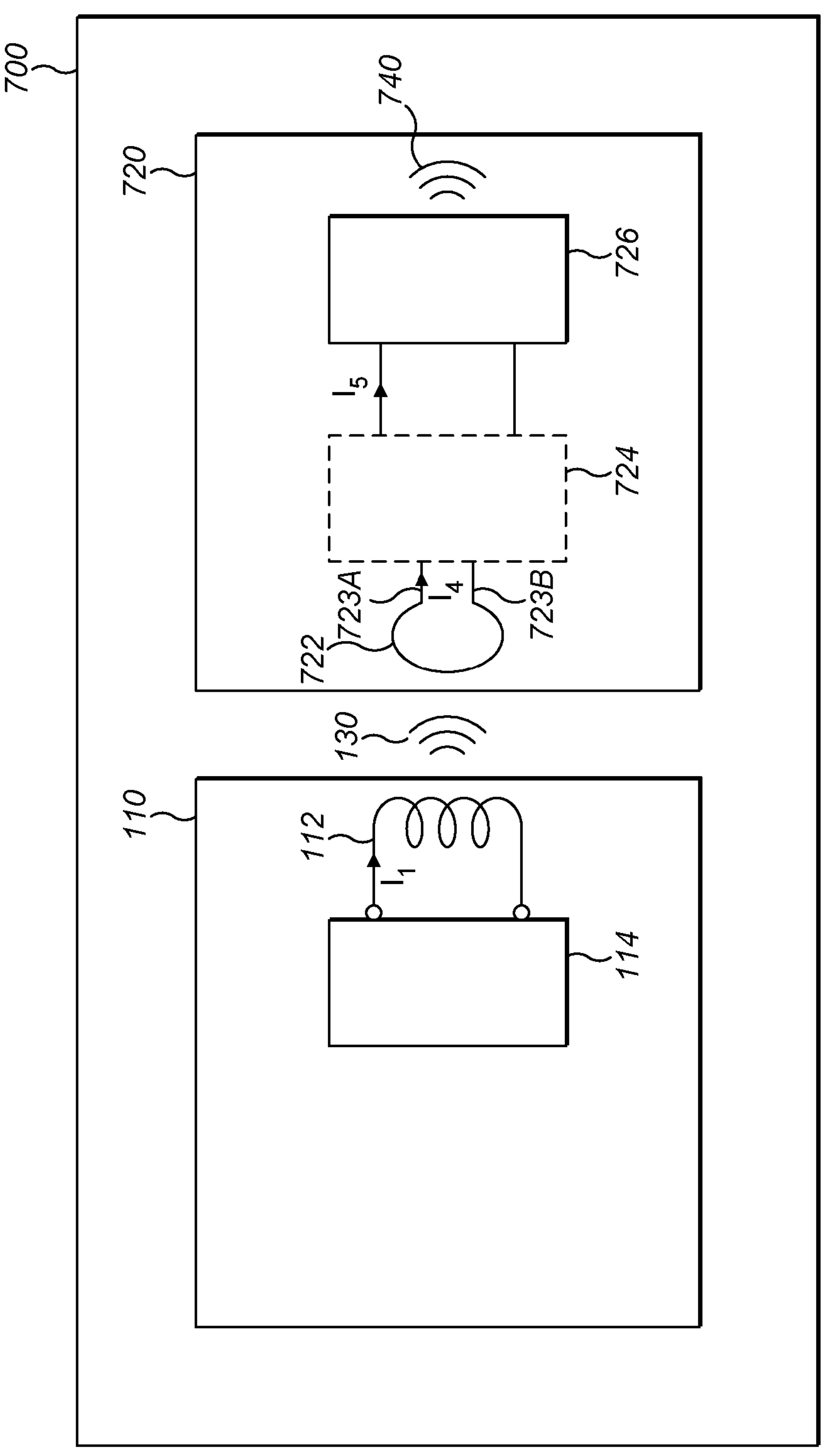
FIG. 7 shows a system comprising a pulsed electromagnetic field therapy device and an ultrasound therapy device according to an alternative example of the present disclosure.

In one alternative example, the light therapy device 120 may be replaced with an ultrasound therapy device. For example, FIG. 7 shows a system 700 comprising the pulsed EMF device 110 and an ultrasound therapy device 720. The pulsed EMF therapy device 110 is configured to generate and emit a pulsed EMF 130 as already described above.

The ultrasound therapy device 720 is configured to emit an ultrasound wave 740 in response to the pulsed EMF 130. In particular, the ultrasound therapy device 720 is configured to convert the pulsed EMF 130 into electrical energy and generate the ultrasound wave 740 based on the electrical energy. Advantageously, the ultrasound therapy device 720 is able to generate and emit the ultrasound wave 740 based on the pulsed EMF 130, without requiring a power source or a power supply.

The ultrasound therapy device 720 comprises a coil loop 722, a conditioning circuit 724 and an ultrasound generating unit 726. The coil loop 722 comprises a first terminal 723A and a second terminal 723B. The conditioning circuit 724 is electrically coupled to the coil loop 722. In particular, the conditioning circuit 724 is electrically coupled to the terminals 723A, 723B of the coil loop 722. The ultrasound generating unit 726 is electrically coupled to the conditioning circuit 724. As such, the conditioning circuit 724 is electrically coupled in between the coil loop 722 and the ultrasound generating unit 726.

The coil loop 722 is arranged to be inductively or magnetically coupled to the coil looped inductor 112. As such, the coil loop will induce a voltage or a potential difference across its terminals 723A and 723B in response to the pulsed EMF 130. The induced voltage will be an AC or alternating voltage corresponding to the pulsed EMF 130 and the current $I_1$ in the coil looped inductor 112. In particular, the induced voltage may comprise a sequence of damped or decaying sinusoidal oscillations, in correspondence with the pulsed EMF 130 and the current $I_1$ illustrated in FIG. 4.

The conditioning circuit 724 and the ultrasound generating unit 726 are coupled to the coil loop 722 such that a closed circuit is formed between the terminals 723A and 723B of the coil loop 722. As such, a current $I_4$ is induced through the coil loop 172 in response to the voltage induced across the terminals 723A and 723B.

The conditioning circuit 724 receives the induced voltage and/or current $I_4$ from the coil loop 722. The conditioning circuit 724 is configured to limit and/or control the amount of electrical power provided to the ultrasound generating unit 726. For example, the conditioning circuit 724 may receive the induced voltage and/or current $I_4$ to provide a conditioned voltage and/or current $I_5$ to the ultrasound generating unit 726 that has a reduced electrical power.

As explained below, the ultrasound generating unit 726 comprises an ultrasound transducer. Advantageously, with the conditioning circuit 724, the ultrasound transducer can be operated whilst avoiding damage to the ultrasound transducer. The ultrasound transducer may require a relatively high voltage in order to generate an ultrasound signal. Therefore, the coil loop 722 may comprise a plurality of turns to meet the voltage requirements of the ultrasound transducer. However, this could result in a large power output of the coil loop 722 which has been found to cause damage to the ultrasound transducer. For example, the power output of the coil loop 722 may depend on the intensity of the pulsed EMF 130 (e.g. the energy and/or magnitude of the EM oscillations). The intensity of the pulsed EMF 130 may be controlled by providing user input at the pulsed EMF device 110, or controlled automatically by the pulsed EMF device 110. For a low intensity pulsed EMF 130, the power output of the coil loop 722 may not exceed a maximum power rating of the ultrasound transducer. For higher intensity pulsed EMFs, the power output of the coil loop 722 may exceed the maximum power rating of the ultrasound transducer, and thereby risk causing damage to the transducer.

The conditioning circuit 724 can advantageously be used to reduce the power provided to the ultrasound transducer whilst meeting the high voltage requirements needed to drive the transducer. In particular, the conditioning circuit 724 may non-linearly reduce the power provided to the ultrasound transducer. In some examples the conditioning circuit 724 may operate to non-linearly reduce the power such that the power provided to the transducer is increasingly reduced, attenuated or limited as the power outputted by the coil loop 722 approaches a maximum value. In other examples, the conditioning circuit 724 may reduce or cap the power when the power outputted by the coil loop 722 exceeds a threshold value.

In some examples, the conditioning circuit 724 may also perform impedance matching functions between the coil loop 722 and the ultrasound generating unit 726. Advantageously, impedance matching has been found to improve the efficiency of the ultrasound device 720 and reduce damage to the ultrasound transducer.

The ultrasound generating unit 726 is configured to receive the conditioned voltage and/or current $I_5$ from the conditioning circuit 724. The ultrasound generating unit 726 is further configured to emit an ultrasound wave 740 in response to the conditioned voltage and/or current $I_5$. In particular, the ultrasound generating unit 126 is configured to emit an ultrasound wave 740 that has a power level or intensity that is generally proportional to the conditioned voltage and/or current $I_5$. It should be appreciated that different implementations of the ultrasound generating unit 726 may respond differently to the conditioned voltage and/or current Is.

Figure 8:
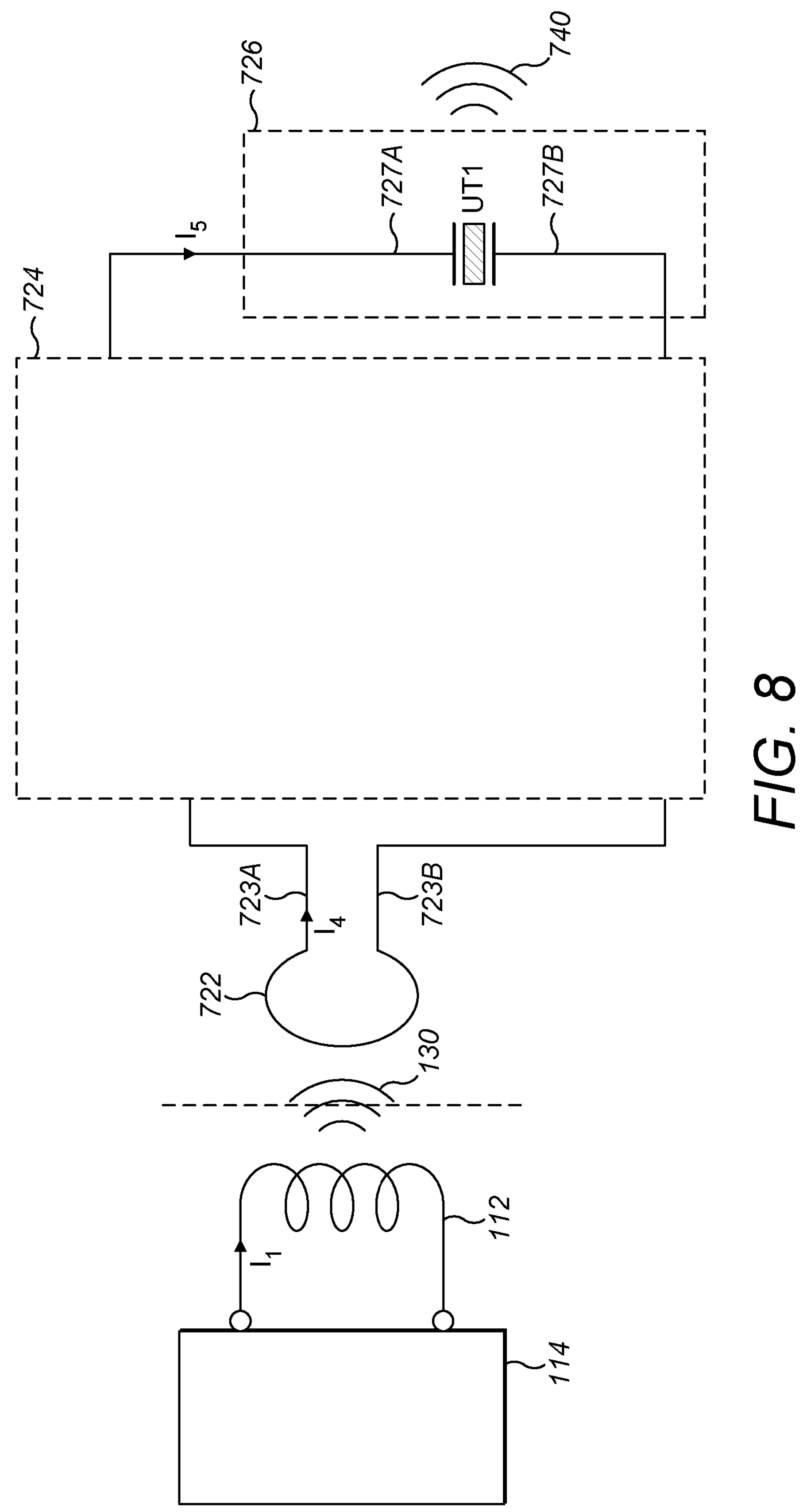
FIG. 8 shows a circuit level diagram of the system of FIG. 7.

As shown in FIG. 8, the ultrasound generating unit 726 comprises an ultrasound transducer UT1. The ultrasound transducer UT1 is configured to emit the ultrasound wave 740 as described above. Optionally, the ultrasound transducer UT1 is self-resonant at the oscillation frequency of the current $I_1$ and the EMF pulse 130. For example, the oscillation frequency of the current $I_1$ and the EMF pulse 130 may be approximately 28 kHz. In this case the ultrasound transducer UT1 is optionally self-resonant at a frequency of 28 kHz. In other examples, the ultrasound transducer UT1 is not self-resonant.

Optionally, the ultrasound transducer UT1 is driven by an AC driving voltage of 50V, 1000V or any voltage between 50-1000V. Optionally, the transducer UT1 is driven by an AC driving voltage of 500V.

The ultrasound generating unit 726 is arranged in the ultrasound therapy device 720 to provide the emitted ultrasound wave 740 to a part of the human or animal body. In particular, the ultrasound transducer UT1 is arranged so that it can be coupled to a part of the body that has been treated with gel, in order to provide the ultrasound wave 740 to that part of the body. In some examples, the ultrasound transducer UT1 is arranged to provide the ultrasound wave 740 to the same part of the body to which the coil looped inductor 112 provides the pulsed EMF 130. In other examples, the ultrasound transducer UT1 is arranged to provide the ultrasound wave 740 to a different part of the body to which the coil looped inductor 122 provides the pulsed EMF 130.

Figure 9:
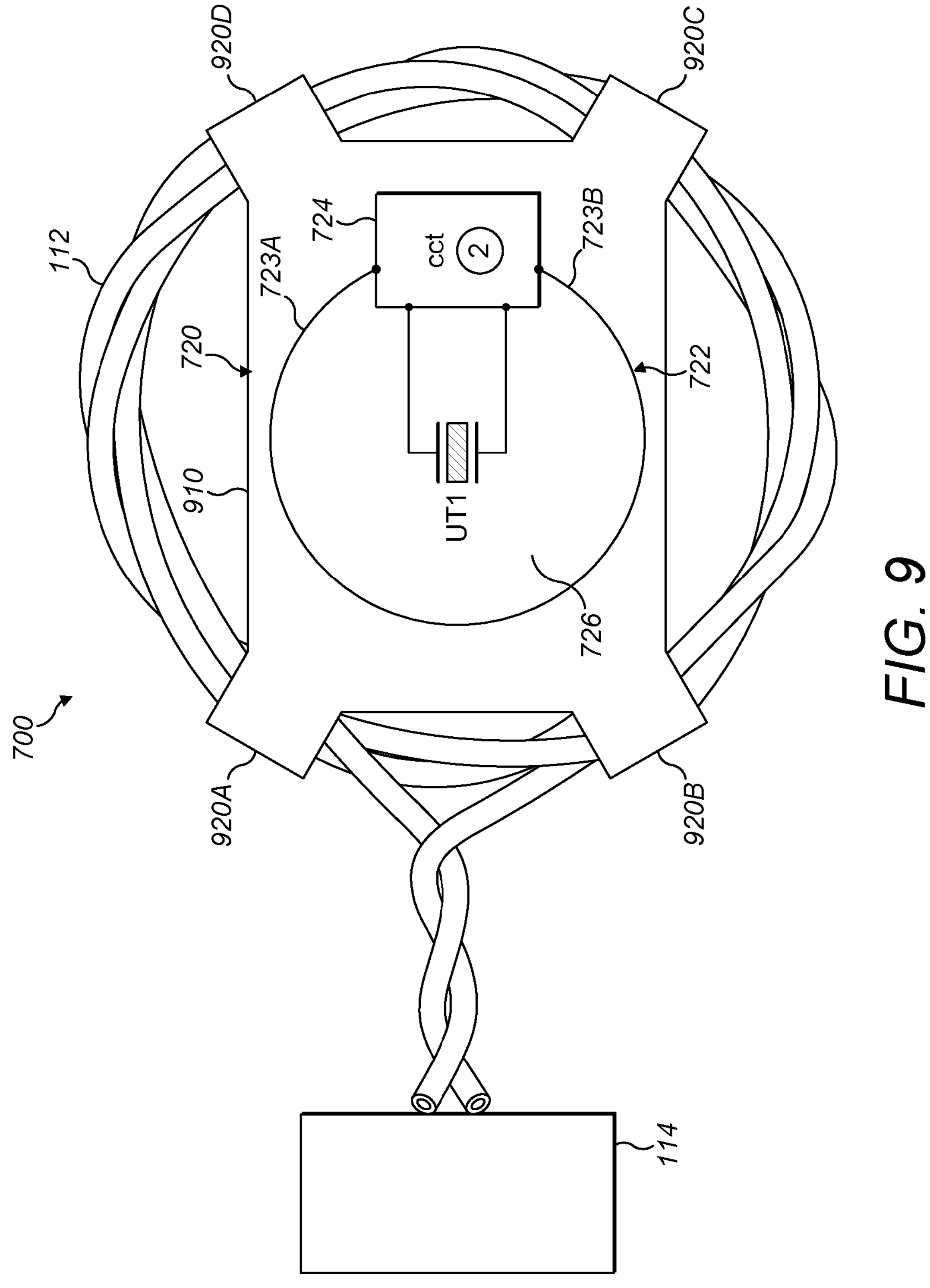
FIG. 9 shows a structural view of the system of FIG. 7.

FIG. 9 illustrates an example structural arrangement of the ultrasound device 726 with respect to the coil looped inductor 112. The system 700 comprises a housing 910. The housing 910 contains or encloses the ultrasound therapy device 720. In particular, the circuitry of the ultrasound therapy device 720, including the coil loop 722, conditioning circuit 724 and ultrasound generating unit 726, are contained in the housing 910. The housing 910 may be shaped and/or dimensioned to be a similar size to the coil looped inductor 112 of the pulsed EMF device 110. For example, the housing may have a length that is the same or less than a diameter of the coil looped inductor 112, and a width that is the same or less than the diameter of the coil looped inductor 112.

The housing 910 comprises a plurality of clips 920A, 920B, 920C and 920D. The clips 920A, 920B, 920C and 920D are configured to secure or attach the housing 910 to the coil looped inductor 112.

FIG. 9 further indicates an example arrangement of the coil loop 722, conditioning circuit 724 and the ultrasound transducer UT1 within the housing 910. The coil loop 722 may be arranged within the housing 910 such that the coil loop 722 is in close proximity to the coil looped inductor 112 when the housing 910 is attached to the coil looped inductor 122. In particular, the coil loop 722 may be arranged such that the coil loop 722 is inductively or magnetically coupled with the coil looped inductor 112. Optionally, as shown in FIG. 9, the coil loop 722 is arranged in the housing 910 so that it shares the same axis as the coil looped inductor 112 when the housing 910 is attached to the coil looped inductor 112. Advantageously, this has been found to improve the inductive coupling between the coil looped inductor 112 and the coil loop 722 and the efficiency of energy transfer between the coil looped inductor 112 and the coil loop 722. However, in other examples, the coil loop 722 may not necessarily share the same axis as the coil looped inductor 112. For example, the coil loop 722 may have an axis that is different to but in parallel with the axis of the coil looped inductor 112. Alternatively, the coil loop 722 may have an axis that is different to and not on parallel with the axis of the coil looped inductor 112.

The ultrasound transducer UT1 may be arranged in the housing 910 such that the ultrasound transducer UT1 emits the ultrasound wave 740 to the same body part to which the coil looped inductor emits the pulsed EMF 130. For example, the ultrasound generating unit 726 may be arranged in the housing 910 to emit the ultrasound wave 740 along the axis of the coil looped inductor 112. Advantageously, by providing the pulsed EMF 130 and the ultrasound wave 740 to the same body part, the pulsed EMF 130 and the ultrasound wave 740 may work together to provide an enhanced physiological effect on the body.

Advantageously, the ultrasound therapy device 720 does not required a power supply in order to supply power to the ultrasound generating unit 726. Rather, the ultrasound generating unit 726 is able to emit the ultrasound wave 740 using electrical energy provided by the pulsed EMF device 110. Furthermore, with the present arrangement, the intensity or waveform peaks of the emitted ultrasound wave 740 may be synchronised with the waveform peaks of the pulsed EMF 130. This may have further advantages in that the effectiveness of the pulsed EMF therapy and the ultrasound therapy is enhanced.

In some examples, the system 700 is contained in a further housing (not shown in FIG. 9). In particular, both the housing 910 and the pulsed EMF device (e.g. the circuitry 114 and the coil looped inductor 112), may be contained in the same common housing. Advantageously, the system 700 may be provided as a single, compact device that is capable of providing both pulsed EMF therapy and ultrasound therapy.

In other examples, the system 700 may not be entirely contained in a single housing. Instead, the pulsed EMF device 110 may be contained in a separate housing (not shown) without the ultrasound therapy device 720. The housing 910 containing the ultrasound therapy device 720 may be configured to attach to the housing containing the pulsed EMF device 110 such that the coil loop 722 is inductively coupled with the coil looped inductor 112 and the ultrasound therapy device 720 operates as described above. As such, in this example, the system 700 may be provided as a modular system comprising a pulsed EMF device with a detachable ultrasound therapy device 720. Advantageously, a user can choose whether or not to use the ultrasound therapy device 720 in combination with the pulsed EMF device 110.

In another example, some of the pulsed EMF device 110 may be comprised in a separate housing (not shown). In particular, the circuitry 114 and other parts of the pulsed EMF device 110 may be comprised in the separate housing, but the coil loop inductor 112 may protrude from, extend from or otherwise be external to the separate housing. As such, the coil looped inductor 112 may be exposed. It will be appreciated that the coil looped inductor 112 can be suitably insulated such that it is safe to touch and operate the pulsed EMF device 110. The housing 910 containing the ultrasound therapy device 720 may be configured to attach to the coil looped inductor 112 as is described above, for example with the clips 920A, 920B, 920C and 920D. Advantageously, the system 700 can be provided as a modular system.

In the illustrated examples, the coil loop 722 comprises one turn. However, in some examples, the coil loop 722 may comprise two or more turns. The number of turns may be a design choice based on the amount of power required in the ultrasound therapy device 720.

In the illustrated examples, the ultrasound therapy device 720 includes one coil loop 722. In alternative examples, the ultrasound therapy device 720 can include two or three coil loops as described above in respect of the light therapy device 120'. For example, the additional coil loop(s) can be coupled in parallel with the coil loop 722 shown in FIG. 8. The coil loops can be arranged in different planes as described above and shown in FIG. 16. Advantageously, the ultrasound therapy device 720 can be used as a wearable device like the light therapy device 120' whilst achieving optimal power transfer between the coil looped inductor 112 and the ultrasound therapy device 720.

In other alternative systems, the light therapy device 120 or the ultrasound therapy device 720 may be replaced with other types of devices. For example, in other example system, the light therapy device 120 or the ultrasound therapy device 720 may be replaced with a negative ion generating device that is powered using the same principles described above.

Example implementations of the pulsed EMF device 110 are described as follows.

Figure 10:
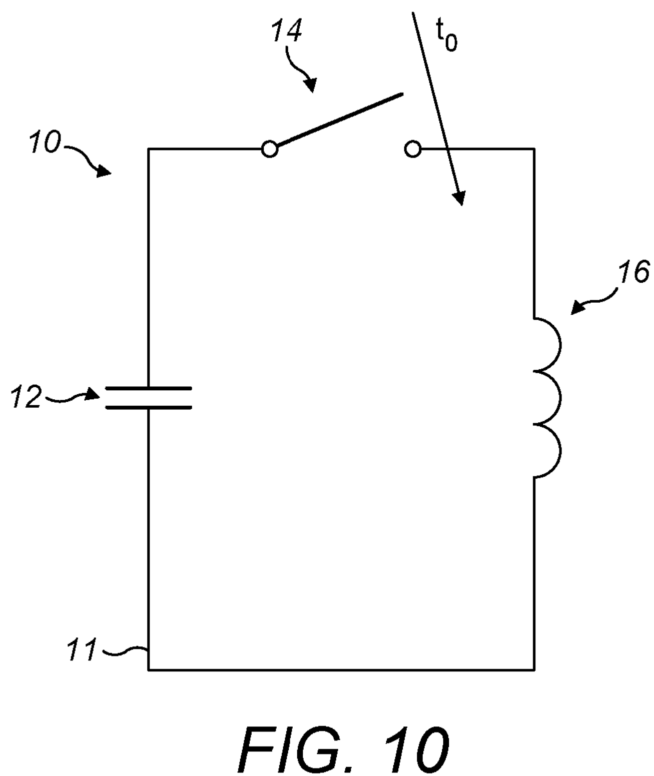
FIG. 10 shows a first example of a pulsed electromagnetic field therapy device for use in the systems of FIGS. 1 and 7.

FIG. 10 is a simplified circuit diagram of a first example of a pulsed electromagnetic field (EMF) therapy device 10. The pulsed electromagnetic field therapy device 10 has a resonant circuit 11 with a capacitor 12 connected to a semiconductor switch 14 and a coil looped inductor 16.

When the semiconductor switch 14 is open, the capacitor 12 is charged from a high voltage circuit (not shown). Closing the semiconductor switch 14 discharges the capacitor 12 into the coil looped inductor 16, initiating oscillation of the resonant circuit 11. With the semiconductor switch 14 closed, the resonant circuit 11 oscillates until losses in the resonant circuit 11 dissipate all of the energy stored in the resonant circuit 11. Thus, when the resonant circuit 11 oscillates, a current comprising a sequence of damped or decaying sinusoidal oscillations will flow through the inductor 16. In response to the current, the inductor 16 will generate and emit a pulsed EMF correspondingly comprising a sequence of damped or decaying sinusoidal oscillations. The above process may be repeated by opening the switch 14 and then closing the switch again to generate further pulses of the pulsed EMF.

The coil looped inductor 16 can be placed adjacent to, or around, a part of the body (such as a limb or joint) where the physiological effect of the pulsed electromagnetic field is desired.

As such, the pulsed EMF device 10 shown in FIG. 10 may be used as the pulsed EMF device 110 described above, whereby the inductor 16 in FIG. 10 corresponds to the coil looped inductor 112 described above.

Figure 11:
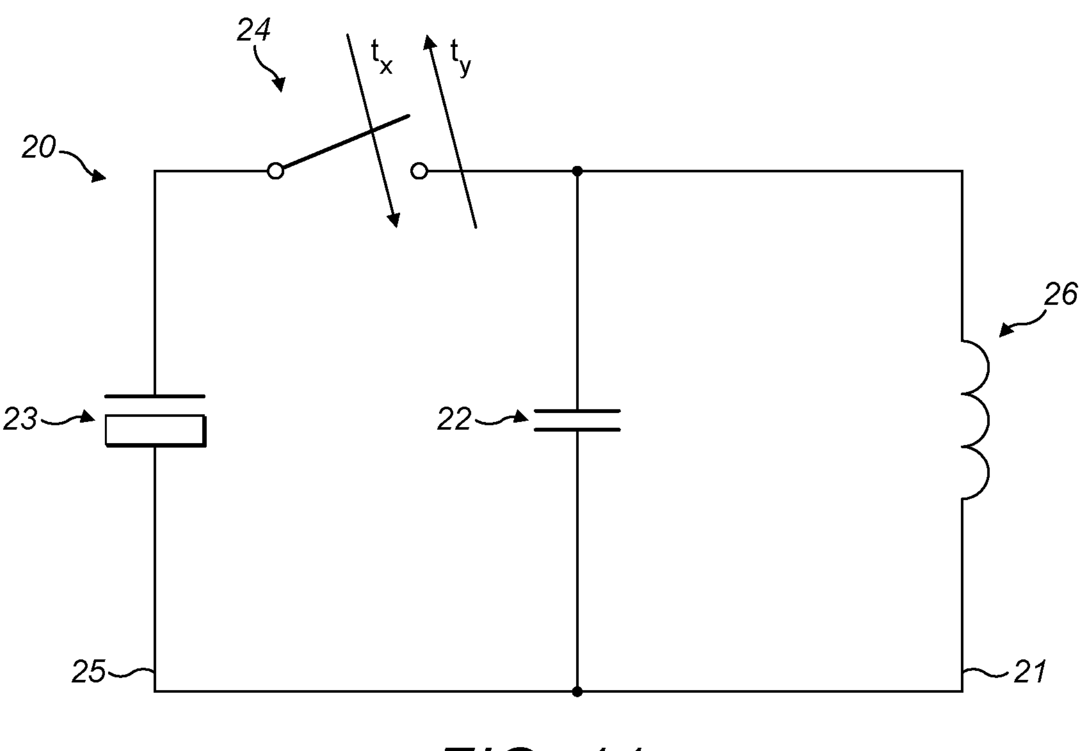
FIG. 11 shows a second example of a pulsed electromagnetic field therapy device for use in the systems of FIGS. 1 and 7.

FIG. 11 illustrates an example of an improved pulsed electromagnetic field therapy device 20.

The pulsed electromagnetic field therapy device 20 has a parallel resonant circuit 21 with a capacitor 22 arranged in parallel with a coil looped inductor 26. A current ramping circuit 25 is external to the parallel resonant circuit 21 and connected in parallel to the parallel resonant circuit 21. The current ramping circuit 25 includes a high current capability capacitor 23 which provides a voltage of around 50 V-350 V (typically 150 V) and a current of around 100 A-2000 A. A semiconductor switch 24 selectively connects the high current capability capacitor 23 to the parallel resonant circuit 21 to ramp-up the current in the coil looped inductor 26.

Figure 12:
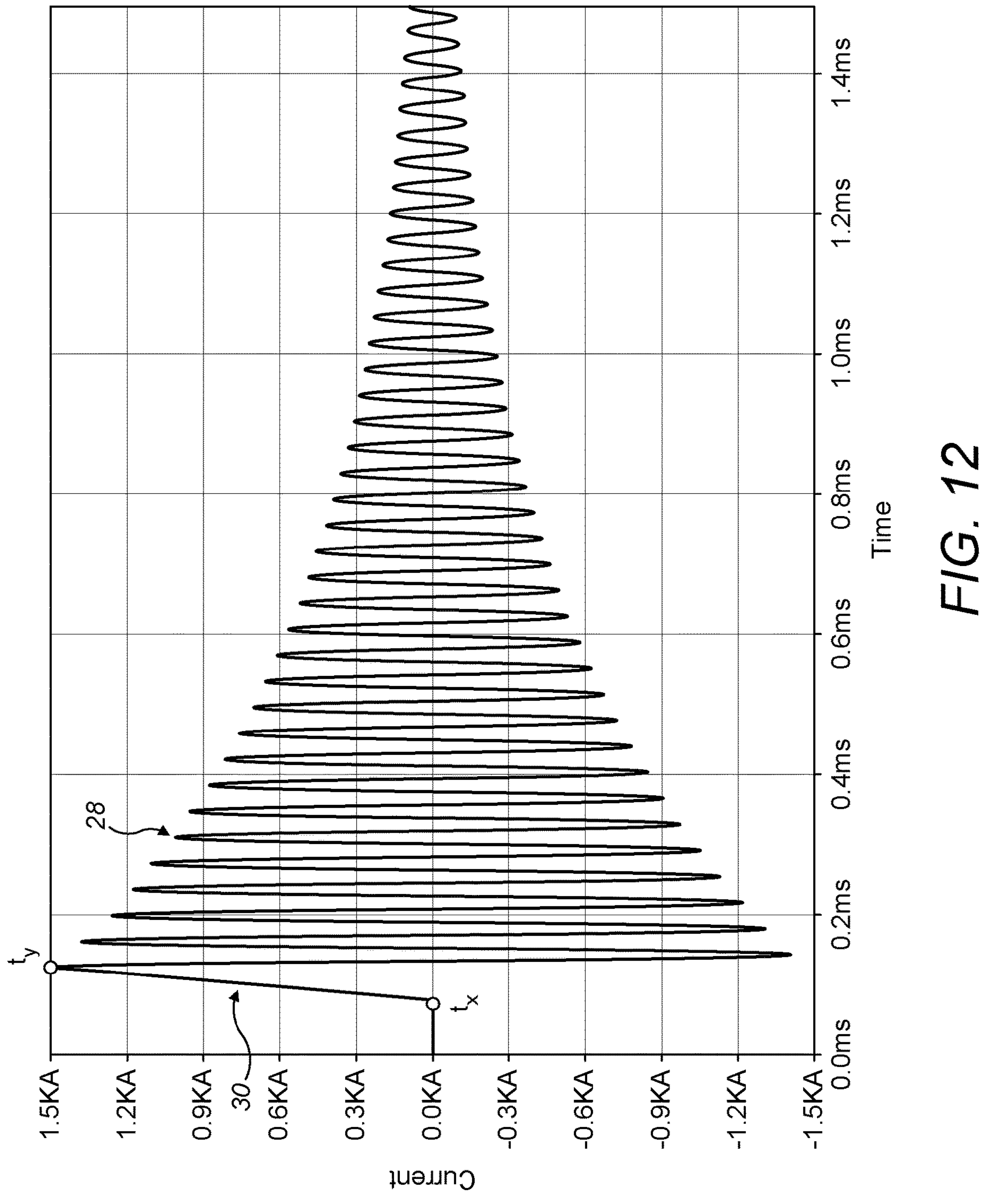
FIG. 12 shows an oscilloscope trace showing current in a resonant circuit of the pulsed electromagnetic field therapy device of FIG. 11, as a function of time.

The oscilloscope trace in FIG. 12 shows the current in the parallel resonant circuit 21 as a function of time. The semiconductor switch 24 is closed at $t_x$ for a current ramping period (indicated by reference numeral 30 in FIG. 12) of about 50 μs to ramp-up the current in the coil looped inductor 26. At the end of the current ramping period at $t_y$, the semiconductor switch 24 is opened, disconnecting the current ramping circuit 25 from the parallel resonant circuit 21 and preventing further increase in the current in the coil looped inductor 26. At the end of the current ramping period, the current in the coil looped inductor 26 has reached a desired current of 1500 A, which is sufficient to produce a pulsed EMF that provides a physiological effect.

At the end of the current ramping period at $t_y$, and with the semiconductor switch 24 open, the current in the coil looped inductor 26 initiates oscillation of the parallel resonant circuit 21. As illustrated by the oscilloscope trace in FIG. 12, the parallel resonant circuit 21 generates a pulsed EMF comprising a sequence of damped sinusoidal oscillations 28 in the coil looped inductor 26. The coil looped inductor 26 is placed adjacent to, or around, a part of the body (such as a limb or joint) where the physiological effect of the pulsed electromagnetic field is desired.

The parallel resonant circuit 21 oscillates until losses in the parallel resonant circuit 21 dissipate all of the energy stored in the parallel resonant circuit 21. To generate more pulses of the pulsed EMF, the above process may be repeated by closing the switch 24 for another current ramping period, and then opening the switch 24.

Advantageously, the semiconductor switch 24 does not need to be a component of the parallel resonant circuit 21 in order to control current within the coil looped inductor 26. Instead, current ramping of the parallel resonant circuit 21 is controlled by current ramping circuit 25 which is external to and connected in parallel to the parallel resonant circuit 21. Not having a semiconductor switch 14 as a component of the parallel resonant circuit 21 provides a number of benefits.

Resistance losses in the parallel resonant circuit 21 are low because the semiconductor switch 24 is external to the parallel resonant circuit 21, so resistance losses from the semiconductor switch 24 are not incurred during oscillation of the parallel resonant circuit 21. As a result, the decay time of the damped oscillations is much longer which increases the time period over which the pulsed electromagnetic field provides a physiological effect for a given initial current in the coil looped inductor 26. For example, a physiological effect may be present when the current in the parallel resonant circuit 21 is greater than around 200 A, and the pulsed electromagnetic field therapy device 20 enjoys a period of around 1100 μs in which the current in the parallel resonant circuit 21 is providing a physiological effect, as compared with only 60 μs with the pulsed electromagnetic field therapy device 10. As a result, the pulsed electromagnetic field therapy device 20 provides a more sustained physiological effect. Moreover, the coil looped inductor 26 need only be ramped to a lower initial current (only 200 A-1500 A in the pulsed electromagnetic field therapy device 20 as compared with 2000 A-3000 A in the pulsed electromagnetic field therapy device 10), leading to lower voltages in the pulsed electromagnetic field therapy device 20 which do not require capacitor 22 or semiconductor switch 24 to be expensive high voltage components, reducing manufacturing costs. Additionally, operating at lower voltages allows capacitor 22 to have a larger capacitance value than a higher voltage capacitor of equivalent physical size, and the selection of a larger capacitance value for capacitor 22 leads to parallel resonant circuit 21 having a lower resonant frequency which allows the pulsed electromagnetic field therapy device 20 to meet regulatory requirements regarding electromagnetic interference.

In the pulsed electromagnetic field therapy device 10, the charge from the capacitor 12 is dumped into the resonant circuit 11 nearly instantaneously when the semiconductor switch 14 in the resonant circuit 11 is closed. This rapid charge discharged into the resonant circuit 11 leads to current reflections which result in significant interference 19. By not having semiconductor switch 24 as a component of the parallel resonant circuit 21, the current in the parallel resonant circuit 21 is increased more gradually over the course of the current ramping period 30. This, combined with the fact that the semiconductor switch 24 is external to and disconnected from the parallel resonant circuit 24 after the current ramping period 30 so that the impedance mismatched semiconductor switch 24 does not lead to reflections, results in a current profile in the parallel resonant circuit 21 which is sinusoidal with low distortion, and which does not show the large amount of interference 19 that may be seen in the pulsed electromagnetic field therapy device 10.

The pulsed EMF device 20 shown in FIG. 11 may be used as the pulsed EMF device 110 described above, whereby the inductor 26 in FIG. 11 corresponds to the coil looped inductor 112 described above.

Figure 13:
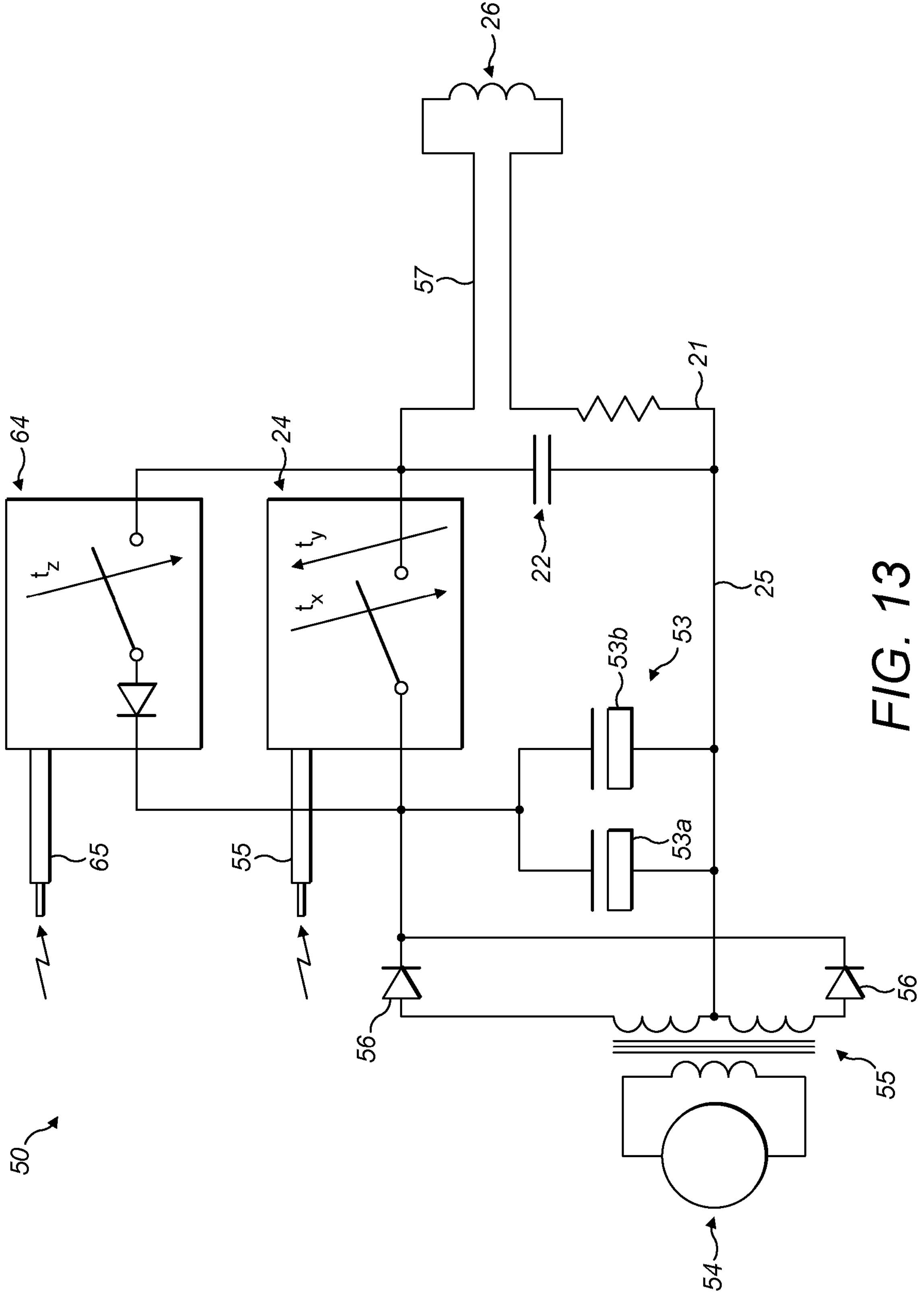
FIG. 13 shows a third example of a pulsed electromagnetic field therapy device for use in the systems of FIGS. 1 and 7.

FIG. 13 illustrates an alternative example of an improved pulsed electromagnetic field therapy device 50. The pulsed electromagnetic field therapy device 50 is generally the same as the pulsed electromagnetic field therapy device 20, with some improvements to electrical safety, charging and control.

The pulsed electromagnetic field may show no significant physiological effect once the current in the parallel resonant circuit 21 has dropped below a certain current (for example, once the current in the parallel resonant circuit 21 has dropped below 200 A). Therefore, a current threshold may be selected based on a current below which little or no significant physiological effect is observed, or below which insufficient physiological effect is observed to meet the needs of a particular physiological or therapeutic application.

Once the current in the parallel resonant circuit 21 has dropped below the current threshold (at a time $t_z$ following time $t_y$), a further switch 64 is closed which connects the parallel resonant circuit 21 to the capacitor bank 53. This substantially reduces oscillation of the parallel resonant circuit 21 and allows at least part of the energy remaining in the parallel resonant circuit 21 to be recycled to at least partially recharge the capacitor bank 53. This saves considerable energy that might otherwise be wasted generating a pulsed electromagnetic field which provides no physiological effect.

Instead of a single high current capability capacitor 23, the pulsed electromagnetic field therapy device 50 has a capacitor bank 53 which is made up of capacitors 53*a* and 53*b* connected in parallel which together offer a high current capability source. The use of capacitor bank 53 may provide redundancy in case a capacitor 53*a* or 53*b* fails, and may be cheaper than using a single high current capability capacitor 23. The capacitor bank 53 could provide a high current capability source using more than two capacitors. In fact, it may be beneficial for the capacitor bank 53 to combine a large number of cheap, lower value capacitors which are smaller and therefore easier to pack into spare space in a housing.

The capacitor bank 53 is charged from power source 54. In some examples, the power source 54 is fed from a mains electricity supply. However, the power supply 54 may be any electrical power source, such as a mains power supply or a battery. To improve electrical safety, and reduce the risk of a patient or operator receiving an electrical shock from the high voltages and currents present in the current ramping circuit 25 and the parallel resonant circuit 21, the current ramping circuit 25 and the parallel resonant circuit 21 are galvanically isolated from the power source 54 by transformer 55. The transformer 55 is provided with diodes 56 for rectification purposes. Therefore, the inductor 26 and other components of the parallel resonant circuit 21 are floating, and therefore safe to touch even if insulation surrounding the inductor 26, cable 57 or other components is damaged.

To complete the isolation, the semiconductor switch 24 receives switching signals over a fibre optic cable 55 and the optional further switch 64 receives switching signals over a fibre optic cable 65. This helps to reduce induced interference which might occur on an electrical link.

The pulsed EMF device 50 shown in FIG. 12 may be used as the pulsed EMF device 110 described above, whereby the inductor 26 in FIG. 11 corresponds to the coil looped inductor 112 described above.

In the above description, it is described that the current $I_1$ in the PEMF device 110 comprises a sequence of decaying or damped sinusoidal oscillations. However, in alternative examples, the current $I_1$ may not necessarily comprise sinusoidal oscillations. In particular, the current $I_1$ may comprise a sequence of decaying or damped oscillations of a non-sinusoidal shape. For example, the current $I_1$ may comprise a sequence of decaying or damped oscillations having a square, triangular, saw-tooth, or any other shaped oscillating waveform. Consequently, it will be appreciated that pulsed EMF 130 may have a corresponding non-sinusoidal shape, as will the voltages induced across the coil loops 122 or 722. Furthermore, the waveform shapes of the currents and light/ultrasound outputs of the light therapy device 120 and the ultrasound therapy device 720 will differ accordingly.

In the above description, it is described that the light therapy device 120 emits a light pulse having an intensity that is proportional to the energy or oscillations of the EMF pulse 130. In other examples, the light therapy device 120 may emit a light pulse that has a fixed intensity or a predetermined intensity pattern, regardless of the shape of the EMF pulse. The conditioning circuitry 124 may be adapted accordingly to supply current to the light generating unit 126, such that the light generating unit 126 emits the light pulse with a fixed intensity or predetermined intensity pattern.

In the above description, it is described that the diode $D_1$ of the light therapy device 120, as shown in FIG. 2, performs the function of a half-wave rectifier. In alternative examples, the diode D1 may be replaced by a different type of rectifier.

In some examples, the diode D1 may be replaced by a full-wave rectifier. For example, the full-wave rectifier may be a bridge-rectifier. In one example arrangement, the bridge-rectifier may have a first input terminal coupled to the terminal 123A of the coil loop 122, a second input terminal coupled to the terminal 123B of the coil loop 122, a first output terminal coupled to the first sides of the resistors $R_{L1}$ and $R_{S1}$, and a second output terminal coupled to second terminal 127B of the light generating unit 126. The bridge-rectifier may comprise four diodes arranged between the input and the output terminals in a bridge-rectifier configuration. For example: an anode of a first diode is coupled to the first input terminal; a cathode of the first diode is coupled to the first output terminal; an anode of a second diode is coupled to the second output terminal; a cathode of the second diode is coupled to the first input terminal; a cathode of a third diode is coupled to the first input terminal; an anode of the third diode is coupled to the second output terminal; a cathode of a fourth diode is coupled to the second input terminal; an anode of the fourth diode is coupled to the second output terminal.

Alternatively, the full-wave rectifier may be a centre-tapped coil rectifier. In an example arrangement of the light therapy device that uses a centre-tapped coil rectifier, the coil loop 122 may be a centre-tapped coil that is inductively coupled with the coil loop inductor 122 of the PEMF device. A first, upper side of the centre-tapped coil is coupled to an anode of a first diode. A second, lower side of the centre-tapped coil is coupled to an anode of the second diode. Cathodes of the first and the second diodes are coupled together to form a first output terminal of the rectifier. A centre tap of the centre-tapped coil forms a second output terminal of the rectifier. The first output terminal is coupled to the first sides of the resistors $R_{L1}$ and $R_{S1}$. The second output terminal is coupled to the second terminal 127B of the light generating unit.

In some embodiments, the diode D1 may be omitted. As such, with reference to FIG. 2, the terminal 123A of the coil loop 122 may be coupled to the first sides of the resistors $R_{L1}$ and $R_{S1}$. The resistors $R_{L1}$ and $R_{S1}$ may receive an unrectified current from the coil loop 122.

It will be appreciated that the diodes D2 and/or D3 of the light therapy device 120' may be varied in accordance with the above variations discussed in respect of the diode D1. For example, the diode D2 and/or D3 can also be implemented as a type of rectifier different to a half-wave rectifier, such as any type of full-wave rectifier including those discussed above. Moreover, the diode D2 and D3 may be omitted. As such, with reference to FIG. 15, the terminals 123A, 123A' and 123A" of the respective coil loops 122, 122' and 122" may be coupled to the first sides of the resistors $R_{S1}$ and $R_{L1}$. The resistors $R_{L1}$ and $R_{S1}$ may receive an unrectified current from the coil loops 122, 122' and 122".

It will be appreciated that other variations and alternative implementations discussed in respect of the light therapy device 120 may apply to the light therapy device 120'.

There follows a list of numbered clauses defining particular embodiments of the present disclosure. Where a numbered clause refers to an earlier numbered clause then those features may be considered in combination.

1. A pulsed electromagnetic field system comprising:

a pulsed electromagnetic field (EMF) device configured to generate an EMF pulse; and a second device comprising:

a coil loop; and a light generating unit electrically coupled to the coil loop, wherein the coil loop is configured to induce a current in response to the EMF pulse, and wherein the light generating unit is arranged to receive at least some of the induced current and emit a light pulse having an intensity proportional to the received current.

2. The system of clause 1, wherein the EMF pulse comprises a decaying sequence of electromagnetic (EM) oscillations.

3. The system of any preceding clause, wherein the pulsed EMF device comprises an inductor configured to emit the EMF pulse, and wherein the second device comprises means for mounting the second device to the pulsed EMF device such that the coil loop of the second device is inductively coupled with the inductor when the second device is mounted to the pulsed EMF device.

4. The system of clause 3, wherein the mounting means is for mounting the second device to the inductor of the pulsed EMF device such that the coil loop of the second device is inductively coupled with the inductor when the second device is mounted to the inductor.

5. The system of any preceding clause, wherein the second device further comprises a rectifier coupled between the coil loop and the light generating unit, the rectifier configured to at least partly rectify the induced current.

6. The system of clause 5, wherein the second device further comprises an interface circuit coupled between the rectifier and the light generating unit, the interface circuit configured to condition the waveform of the induced current and output a conditioned current, wherein the light generating unit receives the conditioned current.

7. The system of clause 6, wherein the interface circuit comprises:

a low pass filter coupled between the rectifier and the light generating unit, the low pass filter configured to filter a first portion of the induced current to output a low frequency component of the conditioned current comprising a smooth pulse over the duration of the EMF pulse; and a resistive path between the rectifier and the light generating unit in parallel with the low pass filter, the resistive path arranged to conduct a second portion of the induced current to output a high frequency component of the conditioned current comprising a sequence of peaks synchronised with oscillations of the EMF pulse.

8. The system of clause 7, wherein:

the rectifier comprises at least one diode having an anode coupled to a first side of the coil loop, and a cathode;

the low pass filter comprises a first resistor, a second resistor and a capacitor, wherein the first resistor is coupled between the cathode of the diode and the second resistor, the second resistor is coupled between the first resistor and a first side of the light generating unit, and the capacitor coupled between a common node between the first and the second resistors and a second side of the light generating unit; and the resistive path comprises a third resistor coupled between the cathode of the diode and the first side of the light generating unit.

9. The system of any preceding clause, wherein the light generating unit comprises at least one light-emitting diode (LED).

10. The system of clause 9, wherein the LED is configured to emit infrared or red light.

11. The system of any preceding clause, wherein the pulsed EMF device further comprises:

a parallel resonant circuit comprising a capacitor connected in parallel with an inductor without a switch between the capacitor and the inductor in the parallel resonant circuit, wherein the parallel resonant circuit is configured to generate the EMF pulse in the inductor while electrical energy is stored in the parallel resonant circuit, and wherein the inductor is configured to be placed relative to a part of a body to provide the pulsed electromagnetic field to the part of the body;

a power source; and a switch, external to the parallel resonant circuit, which is configured to: selectively connect the parallel resonant circuit to the power source for a current ramping period during which a current in the inductor is increased to reach a desired current, and at the end of the current ramping period disconnect the parallel resonant circuit from the power source by opening the switch, wherein the parallel resonant circuit generates the sequence of damped electromagnetic oscillations in the inductor whilst the switch is open.

12. A method comprising:

providing a coil loop inductively coupled to an inductor of a pulsed EMF device;

generating an EMF pulse in the inductor;

inducing a current in the coil loop in response to the EMF pulse;

receiving at least some of the induced current at a light generating unit electrically coupled to the coil loop; and emitting a light pulse from the light generating unit in response to the received current, the light pulse having an intensity proportional to the received current.

13. The method of clause 12, wherein the EMF pulse comprises a decaying sequence of electromagnetic (EM) oscillations.

14. The method of any of clauses 12 to 13, further comprising at least partly rectifying the induced current using a rectifier coupled in between the coil loop and the light generating unit.

15. The method of clause 14, further comprising conditioning the waveform of the induced current using an interface circuit coupled between the rectifier and the light generating unit, and receiving the conditioned current at the light generating unit.

16. The method of clause 15, wherein conditioning the waveform of the induced current comprises low-pass filtering a portion of the induced current using a low pass filter coupled between the rectifier and the light generating unit, to generate a low frequency component of the conditioned current comprising a smooth pulse over the duration of the EMF pulse.

17. The method of clause 16, wherein conditioning the waveform of the induced current comprises passing a portion of the induced current through a resistive path provided between the rectifier and the light generating unit in parallel with the low-pass filter, to generate a high frequency component of the conditioned current comprising a sequence of peaks synchronised with oscillations of the EMF pulse.

18. The method of clause 17, wherein the amplitude or duration of the low frequency component is dependent on a value of one or more resistors of the low pass filter; and/or wherein the amplitude of the high-frequency component is dependent on a value of a resistor in the resistive path.

19. The method of any of clauses 12 to 18, wherein the light pulse is emitted from at least one light-emitting diode (LED) of the light generating unit.

20. The method of clause 19, wherein the light pulse is infrared or red light.

21. The method of any of clauses 12 to 20, wherein the inductor is comprised in a switchless parallel resonant circuit, and wherein generating the EMF pulse comprises:

ramping a current in the inductor of the switchless parallel resonant circuit to reach a desired current by connecting the parallel resonant circuit with a power supply over a current ramping period; and after the current ramping period, generating a sequence of damped electromagnetic oscillations in the inductor by disconnecting the parallel resonant circuit from the power supply.

22. A device for mounting to a pulsed electromagnetic field (EMF) device, the device comprising:

a coil loop arranged to inductively couple to an inductor of a pulsed EMF device when the device is mounted on the pulsed EMF device; and a light generating unit electrically coupled to the coil loop, wherein the coil loop is configured to induce a current in response to an EMF pulse generated by the inductor coil, and wherein the light generating unit is arranged to receive at least some of the induced current and emit a light pulse having an intensity proportional to the received current.

23. The device of clause 22, wherein the device comprises means for mounting the device to the inductor of the pulsed EMF device such that the coil loop of the device is inductively coupled with the inductor when the second device is mounted to the inductor.

24. The device of any of clauses 22 or 23, wherein the device further comprises:

a rectifier coupled between the coil loop and the light generating unit, the rectifier configured to at least partly rectify the induced current; and optionally, an interface circuit coupled between the rectifier and the light generating unit, the interface circuit configured to condition the waveform of the induced current, wherein the light generating unit receives the conditioned current.

25. The device of clause 24, wherein the interface circuit comprises:

a low pass filter coupled between the rectifier and the light generating unit, the low pass filter configured to output a low frequency component of the conditioned current comprising a smooth pulse over the duration of the EMF pulse; and a resistive path between the rectifier and the light generating unit in parallel with the low pass filter, the resistive path arranged to output a high frequency component of the conditioned current comprising a sequence of peaks synchronised with oscillations of the EMF pulse, optionally wherein:

the rectifier comprises at least one diode having an anode coupled to a first side of the coil loop, and a cathode;

the low pass filter comprises a first resistor, a second resistor and a capacitor, wherein the first resistor is coupled between the cathode of the diode and the second resistor, the second resistor is coupled between the first resistor and a first side of the light generating unit, and the capacitor coupled between a common node between the first and the second resistors and a second side of the light generating unit; and the resistive path comprises a third resistor coupled between the cathode of the diode and the first side of the light generating unit.

There follows another list of numbered clauses defining particular embodiments of the present disclosure. Where a numbered clause refers to an earlier numbered clause then those features may be considered in combination.

101. A pulsed electromagnetic field system comprising:

a pulsed electromagnetic field (EMF) device configured to generate an EMF pulse; and a second device comprising:

a first coil loop; and a light generating unit electrically coupled to the first coil loop, wherein the first coil loop is configured to induce a first current in response to the EMF pulse, and wherein the light generating unit is arranged to receive at least some of the first current and emit a light pulse having an intensity proportional to the received current.

102. The system of clause 101, wherein the EMF pulse comprises a decaying sequence of electromagnetic (EM) oscillations.

103. The system of clause 101 or clause 102, wherein the second device comprises a second coil loop electrically coupled to the light generating unit, wherein the second coil loop is configured to induce a second current in response to the EMF pulse, wherein the light generating unit is arranged to receive at least some of the first current and the second current.

104. The system of clause 103, wherein the first coil loop is arranged in a first plane and the second coil loop is in a second plane that is different to the first plane.

105. The system of clause 104, wherein the first plane and the second plane intersect.

106. The system of clause 104 or clause 105, wherein the first plane and the second plane are substantially orthogonal or perpendicular to one another.

107. The system of any of clauses 103 to 106, wherein the first coil loop has a first number of turns and the second coil loop has a second number of turns different to the first number of turns.

108. The system of any preceding clause, wherein the second device further comprises a first rectifier coupled between the first coil loop and the light generating unit, the first rectifier configured to at least partly rectify the first current.

109. The system of clause 108, wherein the second device further comprises a second rectifier coupled between the second coil loop and the light generating unit, the second rectifier configured to at least partly rectify the second current.

110. The system of clause 109, wherein the first coil loop and the first rectifier are coupled in series between a first common node and a second common node, and wherein the second coil loop and the second rectifier are coupled in series between the first common node and the second common node.

111. The system of clause 110, wherein the second device further comprises an interface circuit coupled between the second common node and the light generating unit, the interface circuit configured to condition the waveform of a sum of the first current and the second current, and output a conditioned current, wherein the light generating unit receives the conditioned current.

112. The system of clause 111, wherein the interface circuit comprises:

a low pass filter coupled between the second common node and the light generating unit, the low pass filter configured to filter a first portion of the sum of first current and the second current to output a low frequency component of the conditioned current comprising a smooth pulse over the duration of the EMF pulse; and a resistive path between the second common node and the light generating unit in parallel with the low pass filter, the resistive path arranged to conduct a second portion of the sum of the first current and the second current to output a high frequency component of the conditioned current comprising a sequence of peaks synchronised with oscillations of the EMF pulse.

113. The system of clause 112, wherein:

the first rectifier comprises at least one diode having an anode coupled to a first side of the first coil loop, and a cathode coupled to the second common node;

the second rectifier comprises at least one diode having an anode coupled to a first side of the second coil loop, and a cathode coupled to the second common node;

the low pass filter comprises a first resistor, a second resistor and a capacitor, wherein the first resistor is coupled between the second common node and the second resistor, the second resistor is coupled between the first resistor and a first side of the light generating unit, and the capacitor coupled between a common node between the first and the second resistors and a second side of the light generating unit; and the resistive path comprises a third resistor coupled between the second common node and the first side of the light generating unit.

114. The system of any preceding clause, wherein the light generating unit comprises at least one light-emitting diode (LED).

115. The system of clause 109, wherein the LED is configured to emit infrared or red light.

116. The system of any of clauses 103 to 115, wherein the second device comprises a third coil loop electrically coupled to the light generating unit, wherein the third coil loop is configured to induce a third current in response to the EMF pulse, wherein the light generating unit is arranged to receive at least some of the first current, the second current and the third current, optionally wherein the third coil loop is arranged in a third plane that is different to the first plane and the second plane, 117. The system of clause 116, wherein the third plane intersects with the first plane and the second plane, optionally wherein the third plane is substantially orthogonal or perpendicular to the first plane and to the second plane.

118. The system of any of clauses 116 of 117, wherein the second device further comprises a third rectifier coupled between the third coil loop and the light generating unit, wherein the third rectifier is configured to at least partly rectify the third current, optionally wherein the interface circuit is configured to condition the waveform of a sum of the first current, the second current and the third current.

119. The system of any preceding clause, wherein the second device comprises means for attaching the second device to a part of a human or an animal body.

120. The system of any preceding clause, wherein the pulsed EMF device further comprises:

a parallel resonant circuit comprising a capacitor connected in parallel with an inductor without a switch between the capacitor and the inductor in the parallel resonant circuit, wherein the parallel resonant circuit is configured to generate the EMF pulse in the inductor while electrical energy is stored in the parallel resonant circuit, and wherein the inductor is configured to be placed relative to a part of a body to provide the pulsed electromagnetic field to the part of the body;

a power source; and a switch, external to the parallel resonant circuit, which is configured to: selectively connect the parallel resonant circuit to the power source for a current ramping period during which a current in the inductor is increased to reach a desired current, and at the end of the current ramping period disconnect the parallel resonant circuit from the power source by opening the switch, wherein the parallel resonant circuit generates the sequence of damped electromagnetic oscillations in the inductor whilst the switch is open.

121. A method comprising:

providing a first coil loop for inductively coupling to an inductor of a pulsed EMF device;

generating an EMF pulse in the inductor;

inducing a first current in the first coil loop in response to the EMF pulse;

receiving at least some of the first current at a light generating unit electrically coupled to the first coil loop; and emitting a light pulse from the light generating unit in response to the received current, the light pulse having an intensity proportional to the received current.

122. The method of clause 121, further comprising:

providing a second coil loop for inductively coupling to the inductor of the pulsed EMF device;

inducing a second current in the second coil loop in response to the EMF pulse; and receiving at least some of the first current and the second current at the light generating unit, wherein the first coil loop is provided in a first plane and the second coil loop is provided in a second plane that is different to the first plane, optionally wherein the first plane and the second plane intersect and/or wherein the first plane and the second plane are substantially perpendicular to one another.

123. A device comprising:

a first coil loop arranged to inductively couple to an inductor of a pulsed electromagnetic field (EMF) device; and a light generating unit electrically coupled to the first coil loop, wherein the first coil loop is configured to induce a first current in response to an EMF pulse generated by the inductor coil, and wherein the light generating unit is arranged to receive at least some of the first current and emit a light pulse having an intensity proportional to the received current.

124. The device of clause 123, further comprising a second coil loop electrically coupled to the light generating unit, wherein the second coil loop is configured to induce a second current in response to the EMF pulse, wherein the light generating unit is arranged to receive at least some of the first current and the second current, wherein the first coil loop is in a first plane and the second coil loop is in a second plane that is different to the first plane, optionally wherein the first plane and the second plane intersect and/or wherein the first plane and the second plane are substantially perpendicular to one another.

125. The device of any of clauses 123 or 124, further comprising means for attaching the second device to a part of a human or an animal body.

There follows another list of numbered clauses defining particular embodiments of the present disclosure. Where a numbered clause refers to an earlier numbered clause then those features may be considered in combination.

1001. A pulsed electromagnetic field system comprising:

a pulsed electromagnetic field (EMF) device configured to generate an EMF pulse; and a second device comprising:

a first coil loop; and a light generating unit electrically coupled to the first coil loop, wherein the first coil loop is configured to induce a first current in response to the EMF pulse, and wherein the light generating unit is arranged to receive at least some of the first current and emit a light pulse having an intensity proportional to the received current.

1002. The system of clause 1001, wherein the EMF pulse comprises a decaying sequence of electromagnetic (EM) oscillations.

1003. The system of any preceding clause, wherein the pulsed EMF device comprises an inductor configured to emit the EMF pulse, and wherein the second device comprises means for mounting the second device to the pulsed EMF device such that the first coil loop of the second device is inductively coupled with the inductor when the second device is mounted to the pulsed EMF device.

1004. The system of clause 1003, wherein the mounting means is for mounting the second device to the inductor of the pulsed EMF device such that the first coil loop of the second device is inductively coupled with the inductor when the second device is mounted to the inductor.

1005. The system of any preceding clause, wherein the second device further comprises a first rectifier coupled between the first coil loop and the light generating unit, the first rectifier configured to at least partly rectify the first current.

1006. The system of clause 1005, wherein the second device further comprises an interface circuit coupled between the first rectifier and the light generating unit, the interface circuit configured to condition the waveform of the first current and output a conditioned current, wherein the light generating unit receives the conditioned current.

1007. The system of clause 1006, wherein the interface circuit comprises:

a low pass filter coupled between the first rectifier and the light generating unit, the low pass filter configured to filter a first portion of the first current to output a low frequency component of the conditioned current comprising a smooth pulse over the duration of the EMF pulse; and a resistive path between the first rectifier and the light generating unit in parallel with the low pass filter, the resistive path arranged to conduct a second portion of the first current to output a high frequency component of the conditioned current comprising a sequence of peaks synchronised with oscillations of the EMF pulse.

1008. The system of clause 1007, wherein:

the first rectifier comprises at least one diode having an anode coupled to a first side of the first coil loop, and a cathode;

the low pass filter comprises a first resistor, a second resistor and a capacitor, wherein the first resistor is coupled between the cathode of the diode and the second resistor, the second resistor is coupled between the first resistor and a first side of the light generating unit, and the capacitor coupled between a common node between the first and the second resistors and a second side of the light generating unit; and the resistive path comprises a third resistor coupled between the cathode of the diode and the first side of the light generating unit.

1009. The system of any preceding clause, wherein the light generating unit comprises at least one light-emitting diode (LED).

1010. The system of clause 1009, wherein the LED is configured to emit infrared or red light.

1011. The system of any preceding clause, wherein the second device comprises a second coil loop electrically coupled to the light generating unit, wherein the second coil loop is configured to induce a second current in response to the EMF pulse, wherein the light generating unit is arranged to receive at least some of the first current and the second current, optionally wherein the first coil loop is arranged in a first plane and the second coil loop is in a second plane that is different to the first plane.

1012. The system of clause 1011, wherein the first plane and the second plane intersect, optionally wherein the first plane and the second plane are substantially orthogonal or perpendicular to one another.

1013. The system of any of clauses 1011 to 1012, wherein the second device further comprises a second rectifier coupled between the second coil loop and the light generating unit, the second rectifier configured to at least partly rectify the second current, optionally wherein the interface circuit is configured to condition the waveform of a sum of the first current and the second current.

1014. The system of any of clauses 1011 to 1013, wherein the second device comprises a third coil loop electrically coupled to the light generating unit, wherein the third coil loop is arranged in a third plane that is different to the first plane and the second plane, optionally wherein the third plane intersects with the first plane and the second plane.

1015. The system of any preceding clause, wherein the second device comprises means for attaching the second device to a part of a human or an animal body.

1016. The system of any preceding clause, wherein the pulsed EMF device further comprises:

a parallel resonant circuit comprising a capacitor connected in parallel with an inductor without a switch between the capacitor and the inductor in the parallel resonant circuit, wherein the parallel resonant circuit is configured to generate the EMF pulse in the inductor while electrical energy is stored in the parallel resonant circuit, and wherein the inductor is configured to be placed relative to a part of a body to provide the pulsed electromagnetic field to the part of the body;

a power source; and a switch, external to the parallel resonant circuit, which is configured to: selectively connect the parallel resonant circuit to the power source for a current ramping period during which a current in the inductor is increased to reach a desired current, and at the end of the current ramping period disconnect the parallel resonant circuit from the power source by opening the switch, wherein the parallel resonant circuit generates the sequence of damped electromagnetic oscillations in the inductor whilst the switch is open.

1017. A method comprising:

providing a first coil loop for inductively coupling to an inductor of a pulsed EMF device;

generating an EMF pulse in the inductor;

inducing a first current in the first coil loop in response to the EMF pulse;

receiving at least some of the first current at a light generating unit electrically coupled to the first coil loop; and emitting a light pulse from the light generating unit in response to the received current, the light pulse having an intensity proportional to the received current.

1018. The method of clause 1017, wherein the EMF pulse comprises a decaying sequence of electromagnetic (EM) oscillations.

1019. The method of any of clauses 1017 to 1018, further comprising at least partly rectifying the first current using a first rectifier coupled in between the first coil loop and the light generating unit.

1020. The method of clause 1019, further comprising conditioning the waveform of the first current using an interface circuit coupled between the first rectifier and the light generating unit, and receiving the conditioned current at the light generating unit.

1021. The method of clause 1020, wherein conditioning the waveform of the first current comprises low-pass filtering a portion of the first current using a low pass filter coupled between the first rectifier and the light generating unit, to generate a low frequency component of the conditioned current comprising a smooth pulse over the duration of the EMF pulse.

1022. The method of clause 1021, wherein conditioning the waveform of the first current comprises passing a portion of the first current through a resistive path provided between the first rectifier and the light generating unit in parallel with the low-pass filter, to generate a high frequency component of the conditioned current comprising a sequence of peaks synchronised with oscillations of the EMF pulse.

1023. The method of clause 1022, wherein the amplitude or duration of the low frequency component is dependent on a value of one or more resistors of the low pass filter; and/or wherein the amplitude of the high-frequency component is dependent on a value of a resistor in the resistive path.

1024. The method of any of clauses 1017 to 1023, wherein the light pulse is emitted from at least one light-emitting diode (LED) of the light generating unit.

1025. The method of clause 1024, wherein the light pulse is infrared or red light.

1026. The method of any of clauses 1017 to 1025, further comprising:

providing a second coil loop for inductively coupling to the inductor of the pulsed EMF device;

inducing a second current in the second coil loop in response to the EMF pulse; and receiving at least some of the first current and the second current at the light generating unit, wherein the first coil loop is provided in a first plane and the second coil loop is provided in a second plane that is different to the first plane, optionally wherein the first plane and the second plane intersect and/or wherein the first plane and the second plane are substantially orthogonal or perpendicular to one another.

1027. The method of clause 1026, further comprising at least partly rectifying the second current using a second rectifier coupled in between the second coil loop and the light generating unit, optionally wherein the method further comprises: conditioning the waveform of a sum of the first current and the second current using an interface circuit coupled between the first and the second rectifiers and the light generating unit, and receiving the conditioned current at the light generating unit.

1028. The method of any of clauses 1026 to 1027, further comprising providing a third coil loop for inductively coupling to the inductor of the pulsed EMF device, wherein the third coil loop is in a third plane that is different to the first plane and the second plane, optionally wherein the third plane intersects with the first plane and the second plane.

1029. The method of any of clauses 1017 to 1028, wherein the inductor is comprised in a switchless parallel resonant circuit, and wherein generating the EMF pulse comprises:

ramping a current in the inductor of the switchless parallel resonant circuit to reach a desired current by connecting the parallel resonant circuit with a power supply over a current ramping period; and after the current ramping period, generating a sequence of damped electromagnetic oscillations in the inductor by disconnecting the parallel resonant circuit from the power supply.

1030. A device comprising:

a first coil loop arranged to inductively couple to an inductor of a pulsed electromagnetic field (EMF) device; and a light generating unit electrically coupled to the coil loop, wherein the first coil loop is configured to induce a first current in response to an EMF pulse generated by the inductor coil, and wherein the light generating unit is arranged to receive at least some of the first current and emit a light pulse having an intensity proportional to the received current.

1031. The device of clause 1030, wherein the device comprises means for mounting the device to the inductor of the pulsed EMF device such that the first coil loop of the device is inductively coupled with the inductor when the second device is mounted to the inductor.

1032. The device of any of clauses 1030 or 1031, wherein the device further comprises:

a first rectifier coupled between the first coil loop and the light generating unit, the first rectifier configured to at least partly rectify the first current; and optionally, an interface circuit coupled between the first rectifier and the light generating unit, the interface circuit configured to condition the waveform of the first current, wherein the light generating unit receives the conditioned current.

1033. The device of clause 1032, wherein the interface circuit comprises:

a low pass filter coupled between the first rectifier and the light generating unit, the low pass filter configured to output a low frequency component of the conditioned current comprising a smooth pulse over the duration of the EMF pulse; and a resistive path between the first rectifier and the light generating unit in parallel with the low pass filter, the resistive path arranged to output a high frequency component of the conditioned current comprising a sequence of peaks synchronised with oscillations of the EMF pulse, optionally wherein:

the first rectifier comprises at least one diode having an anode coupled to a first side of the first coil loop, and a cathode;

the low pass filter comprises a first resistor, a second resistor and a capacitor, wherein the first resistor is coupled between the cathode of the diode and the second resistor, the second resistor is coupled between the first resistor and a first side of the light generating unit, and the capacitor coupled between a common node between the first and the second resistors and a second side of the light generating unit; and the resistive path comprises a third resistor coupled between the cathode of the diode and the first side of the light generating unit.

1034. The device of any of clauses 1030 to 1033, further comprising a second coil loop electrically coupled to the light generating unit, wherein the second coil loop is configured to induce a second current in response to the EMF pulse, wherein the light generating unit is arranged to receive at least some of the first current and the second current, wherein the first coil loop is in a first plane and the second coil loop is in a second plane that is different to the first plane, optionally wherein the first plane and the second plane intersect and/or wherein the first plane and the second plane are substantially orthogonal or perpendicular to one another.

1035. The device of clause 1034, further comprising a second rectifier coupled between the second coil loop and the light generating unit, the second rectifier configured to at least partly rectify the second current, optionally wherein the interface circuit is configured to condition the waveform of a sum of the first current and the second current.

1036. The device of any of clauses 1034 to 1035, further comprising a third coil loop electrically coupled to the light generating unit, wherein the third coil loop is in a third plane different to the first plane and the second plane, optionally wherein the third plane intersects with the first plane and the second plane.

1037. The device of any of clauses 1030 to 1036, further comprising means for attaching the second device to a part of a human or an animal body.

The invention claimed is:

1. A pulsed electromagnetic field system comprising:

a pulsed electromagnetic field (EMF) device configured to generate an EMF pulse; and a second device comprising:

a first coil loop; and a light generating unit electrically coupled to the first coil loop, wherein the first coil loop is configured to induce a first current in response to the EMF pulse, wherein the light generating unit is arranged to receive at least some of the first current and emit a light pulse having an intensity proportional to the received current, wherein the second device comprises a second coil loop electrically coupled to the light generating unit, wherein the second coil loop is configured to induce a second current in response to the EMF pulse, wherein the light generating unit is arranged to receive at least some of the first current and the second current, and wherein the first coil loop is arranged in a first plane and the second coil loop is in a second plane that is different to the first plane.

2. The system of claim 1, wherein the EMF pulse comprises a decaying sequence of electromagnetic (EM) oscillations.

3. The system of claim 1, wherein the second device further comprises a first rectifier coupled between the first coil loop and the light generating unit, the first rectifier configured to at least partly rectify the first current.

4. The system of claim 3, wherein the second device further comprises an interface circuit coupled between the first rectifier and the light generating unit, the interface circuit configured to condition the waveform of the first current and output a conditioned current, wherein the light generating unit receives the conditioned current.

5. The system of claim 4, wherein the interface circuit comprises:

a low pass filter coupled between the first rectifier and the light generating unit, the low pass filter configured to filter a first portion of the first current to output a low frequency component of the conditioned current comprising a smooth pulse over the duration of the EMF pulse; and a resistive path between the first rectifier and the light generating unit in parallel with the low pass filter, the resistive path arranged to conduct a second portion of the first current to output a high frequency component of the conditioned current comprising a sequence of peaks synchronised with or corresponding to oscillations of the EMF pulse, optionally wherein:

the first rectifier comprises at least one diode having an anode coupled to a first side of the first coil loop, and a cathode;

the low pass filter comprises a first resistor, a second resistor and a capacitor, wherein the first resistor is coupled between the cathode of the diode and the second resistor, the second resistor is coupled between the first resistor and a first side of the light generating unit, and the capacitor coupled between a common node between the first and the second resistors and a second side of the light generating unit; and the resistive path comprises a third resistor coupled between the cathode of the diode and the first side of the light generating unit.

6. The system of claim 1, wherein the light generating unit comprises at least one light-emitting diode (LED), optionally wherein the LED is configured to emit infrared or red light.

7. The system of claim 1, wherein one or more of the following applies:

the first plane and the second plane intersect;

the first plane and the second plane are substantially orthogonal or perpendicular to one another; and the first coil loop has a first number of turns and the second coil loop has a second number of turns different to the first number of turns.

8. A method comprising:

providing a first coil loop configured to inductively couple to an inductor of a pulsed EMF device, wherein the first coil is arranged in a first plane;

providing a second coil loop in a second plane that is different to a first plane;

generating an EMF pulse in the inductor;

inducing a first current in the first coil loop in response to the EMF pulse;

inducing a second current in the second coil in response to the EMF pulse;

receiving at least some of the first current and the second current at a light generating unit electrically coupled to the first coil loop and the second coil loop; and emitting a light pulse from the light generating unit in response to the received current, the light pulse having an intensity proportional to the received current.

9. The method of claim 8, wherein the EMF pulse comprises a decaying sequence of electromagnetic (EM) oscillations.

10. The method of claim 8, further comprising at least partly rectifying the first current using a first rectifier coupled in between the first coil loop and the light generating unit.

11. The method of claim 10, further comprising conditioning the waveform of the first current using an interface circuit coupled between the first rectifier and the light generating unit, and receiving the conditioned current at the light generating unit.

12. The method of claim 11, wherein conditioning the waveform of the first current comprises low-pass filtering a portion of the first current using a low pass filter coupled between the first rectifier and the light generating unit, to generate a low frequency component of the conditioned current comprising a smooth pulse over the duration of the EMF pulse.

13. The method of claim 12, wherein conditioning the waveform of the first current comprises passing a portion of the first current through a resistive path provided between the first rectifier and the light generating unit in parallel with the low-pass filter, to generate a high frequency component of the conditioned current comprising a sequence of peaks synchronised with or corresponding to oscillations of the EMF pulse, optionally wherein:

the amplitude or duration of the low frequency component is dependent on a value of one or more resistors of the low pass filter; and/or the amplitude of the high-frequency component is dependent on a value of a resistor in the resistive path.

14. The method of claim 8, wherein the light pulse is emitted from at least one light-emitting diode (LED) of the light generating unit, optionally wherein the light pulse is infrared or red light.

15. A device comprising:

a first coil loop configured to inductively couple to an inductor of a pulsed electromagnetic field (EMF) device; and a light generating unit electrically coupled to the coil loop, wherein the first coil loop is configured to induce a first current in response to an EMF pulse generated by the inductor coil, wherein the light generating unit is arranged to receive at least some of the first current and emit a light pulse having an intensity proportional to the received current wherein the device further comprises a second coil loop electrically coupled to the light generating unit, wherein the second coil loop is configured to induce a second current in response to the EMF pulse, wherein the light generating unit is arranged to receive at least some of the first current and the second current, and wherein the first coil loop is arranged in a first plane and the second coil loop is in a second plane that is different to the first plane.

16. The device of claim 15, wherein the device further comprises:

a first rectifier coupled between the first coil loop and the light generating unit, the first rectifier configured to at least partly rectify the first current; and optionally, an interface circuit coupled between the first rectifier and the light generating unit, the interface circuit configured to condition the waveform of the first current, wherein the light generating unit receives the conditioned current.

17. The device of claim 16, wherein the interface circuit comprises:

a low pass filter coupled between the first rectifier and the light generating unit, the low pass filter configured to output a low frequency component of the conditioned current comprising a smooth pulse over the duration of the EMF pulse; and a resistive path between the first rectifier and the light generating unit in parallel with the low pass filter, the resistive path arranged to output a high frequency component of the conditioned current comprising a sequence of peaks synchronised with or corresponding to oscillations of the EMF pulse, optionally wherein:

the first rectifier comprises at least one diode having an anode coupled to a first side of the first coil loop, and a cathode;

the low pass filter comprises a first resistor, a second resistor and a capacitor, wherein the first resistor is coupled between the cathode of the diode and the second resistor, the second resistor is coupled between the first resistor and a first side of the light generating unit, and the capacitor coupled between a common node between the first and the second resistors and a second side of the light generating unit; and the resistive path comprises a third resistor coupled between the cathode of the diode and the first side of the light generating unit.

* * * * *